(12) United States Patent
Kawamura

(10) Patent No.: US 6,867,046 B2
(45) Date of Patent: Mar. 15, 2005

(54) METHOD FOR MEASURING CONCENTRATION OF SOLUTION AND METHOD OF URINALYSIS USING THE SAME

(75) Inventor: Tatsurou Kawamura, Kyotanabe (JP)

(73) Assignee: Matsushita Electric Industrial Co., Ltd., Osaka (JP)

(*) Notice: Subject to any disclaimer, the term of this patent is extended or adjusted under 35 U.S.C. 154(b) by 404 days.

(21) Appl. No.: 09/739,226

(22) Filed: Dec. 19, 2000

(65) Prior Publication Data
US 2001/0005593 A1 Jun. 28, 2001

(30) Foreign Application Priority Data
Dec. 21, 1999 (JP) .......................................... 11-363156

(51) Int. Cl.[7] .............................................. G01N 33/00
(52) U.S. Cl. ........................................ 436/86; 436/164
(58) Field of Search ................................. 436/86, 164

(56) References Cited

U.S. PATENT DOCUMENTS

| | | | |
|---|---|---|---|
| 4,090,919 A | | 5/1978 | Chibata et al. |
| 4,201,471 A | | 5/1980 | Pitt et al. |
| 4,203,724 A | | 5/1980 | Sawai et al. |
| 4,485,176 A | * | 11/1984 | Bollin et al. ................ 436/86 |
| 4,684,252 A | | 8/1987 | Makiguchi et al. |
| 4,766,080 A | * | 8/1988 | Fleming ....................... 436/74 |
| 5,100,805 A | | 3/1992 | Ziege et al. |
| 5,104,527 A | | 4/1992 | Clinkenbeard |
| 5,178,831 A | | 1/1993 | Sakota et al. .............. 422/56 |
| 5,212,099 A | | 5/1993 | Marcus |
| 5,264,589 A | * | 11/1993 | Corey .......................... 548/511 |
| 5,328,850 A | * | 7/1994 | Corey .......................... 436/86 |
| 5,478,748 A | * | 12/1995 | Akins et al. ................. 436/86 |
| 5,543,018 A | | 8/1996 | Stevens et al. |
| 5,922,609 A | * | 7/1999 | Kellner et al. ............. 436/103 |
| 6,036,922 A | | 3/2000 | Kawamura et al. |
| 6,297,057 B1 | * | 10/2001 | Kawamura et al. ......... 436/86 |

FOREIGN PATENT DOCUMENTS

| | | |
|---|---|---|
| EP | 0751388 A2 A3 | 1/1997 |
| EP | 0805352 A1 | 11/1997 |
| EP | 0845673 A2 A3 | 6/1998 |
| GB | 755 900 | 8/1956 |
| GB | 1 600 139 | 10/1981 |
| JP | 58 209946 | 12/1983 |
| JP | 07 138119 | 5/1995 |
| JP | 9-145605 | 6/1997 |
| JP | 11133022 | 5/1999 |

* cited by examiner

*Primary Examiner*—Monique T. Cole
(74) *Attorney, Agent, or Firm*—McDermott Will & Emery LLP

(57) ABSTRACT

The present invention provides a method for measuring concentration of a solution, in which an acid is mixed in a sample to be detected to reduce the variations in pH, and the mixture is heated up to not more than 80° C. to measure the transmitted light and/or scattered light power. The present invention also provides a method of urinalysis in which the protein concentration is measured after measuring the angle of rotation. Herewith, in the method in which the sample to be detected is heated to coagulate protein, and the protein concentration is measured from the degree of opacification resulting therefrom, it is possible to reduce the influence of the pH of the sample to be detected, and to decrease the heating temperature.

20 Claims, 9 Drawing Sheets

F I G. 3
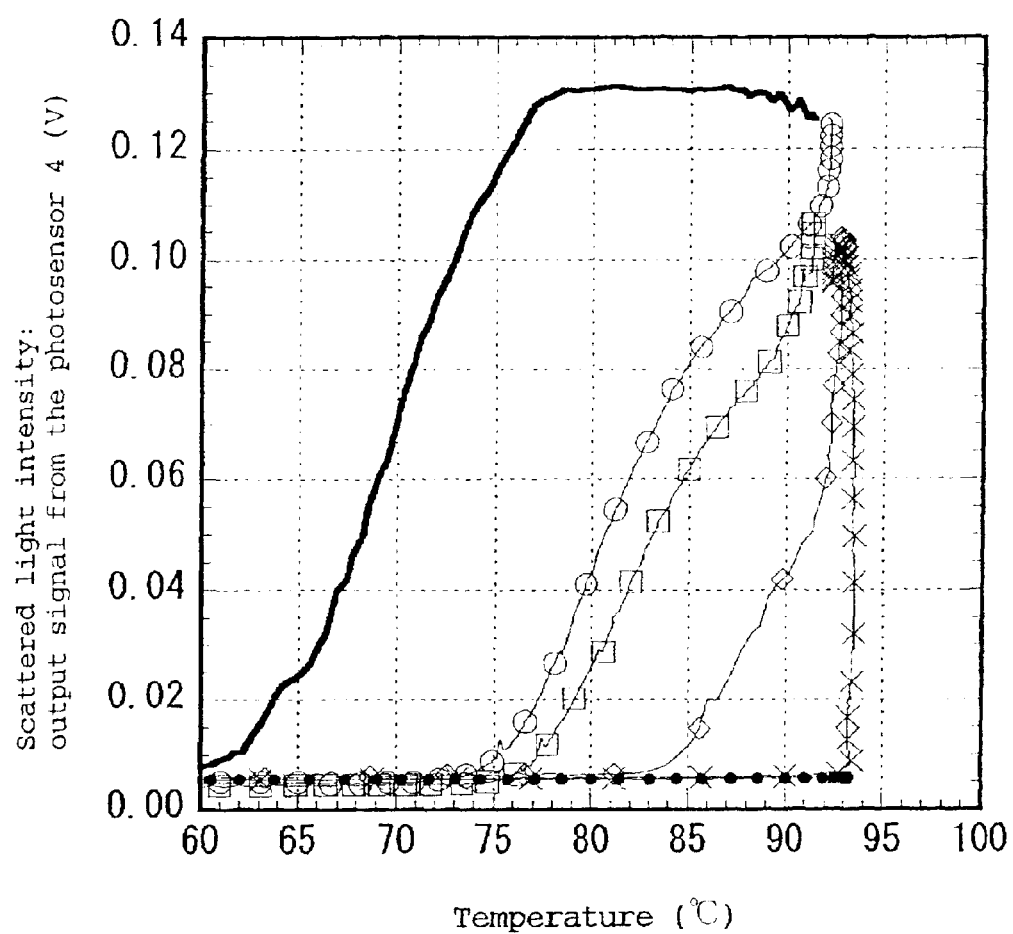

F I G. 6
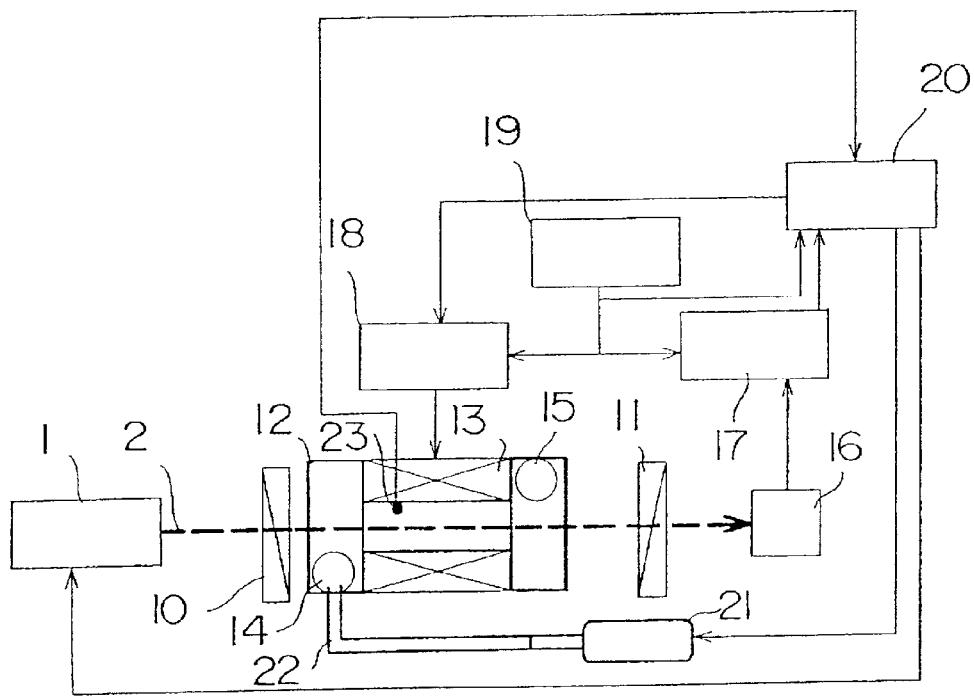

F I G. 10
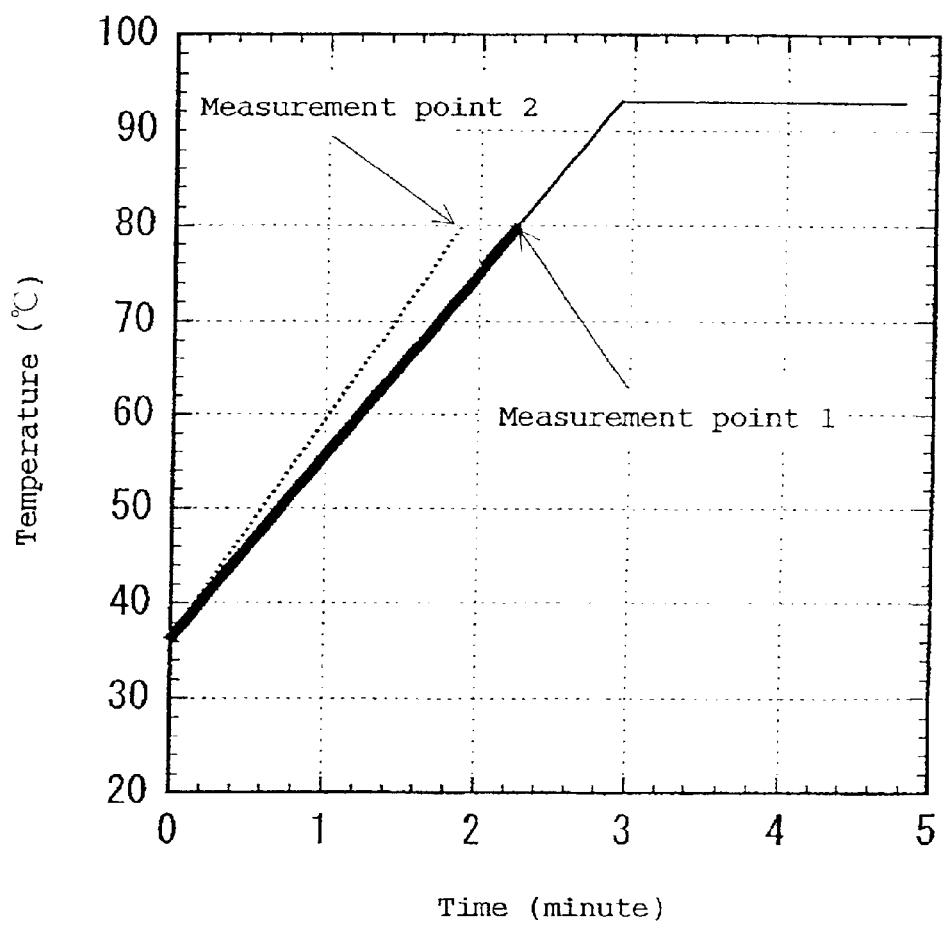

METHOD FOR MEASURING CONCENTRATION OF SOLUTION AND METHOD OF URINALYSIS USING THE SAME

BACKGROUND OF THE INVENTION

The present invention relates to a method for measuring the concentration of a specific component contained in a sample to be detected, and a measuring apparatus thereof. More particularly, the present invention relates to a method for measuring the concentration of protein, and the concentration of glucose in a urine collected from a human, or other animals.

The glucose concentration in a urine (i.e., urine sugar value) and the protein concentration in a urine (i.e., urine protein value) reflect a part of the health condition. Then, there has been a demand for an easy and accurate measuring method thereof.

A conventional urinalysis has been accomplished in the following manner. That is, a test paper impregnated with a reagent corresponding to each inspection item such as sugar or protein is dipped in a urine. Then, the color reaction of the test paper is observed by means of a spectrophotometer or the like. With this method, a different test paper is required for each inspection item, and a new test paper is required for every inspection. Therefore, there has occurred a problem of a high running cost. Further, there has also been a limit as to the automation of a urinalysis for laborsaving.

Especially when such test papers are used at home, an amateur is required to perform setting and exchanging of the test papers. This operation is relatively complicated, and disliked, thus inhibiting an urinalysis apparatus from coming into widespread use at home.

In contrast, in PCT International Publication No. 97/18470, there is proposed a method of urinalysis requiring no consumable items such as test papers. This method is based on the notice that glucose and albumin exhibit optical activities, while the other urine components exhibit almost no optical activities. Namely, with this method of urinalysis, the urine sugar value and the urine protein value are determined by measuring the angle of rotation of the urine.

When a light is propagated in a liquid containing an optical active substance, the polarization direction of the light rotates in proportion to the concentration of the optical active substance. That is, the formula (1):

$$A = L \times \alpha \quad (1)$$

where L denotes a measured optical path length, A denotes an angle of rotation (degree), and α denotes a specific rotatory power is satisfied.

For example, when a light with a wavelength of 589 nm is propagated 100 mm in an aqueous glucose solution with a concentration of 100 mg/dl, the polarization direction of the light rotates $50 \times 10^{-3}$ degrees. By utilizing such characteristics, it is possible to determine the urine sugar value and the urine protein value from the formula (1). Herein, the respective specific rotatory powers of glucose and albumin at 20° C. are shown in Table 1.

TABLE 1

| | | Wavelength (nm) | |
|---|---|---|---|
| | | 589 | 670 |
| Specific rotatory power (degree) | Glucose | 50 | 40 |
| | Albumin | −60 | −40 |

When N types of optical active substances are contained in the liquid, the formula (1) is reexpressed as the following formula (2):

$$A = L \times (\alpha 1 \times C1 + \alpha 2 \times C2 + \ldots + \alpha N \times CN) \quad (2)$$

where L denotes a measured optical path length, A denotes an angle of rotation (degree), and αN denotes the specific rotatory power of a substance "n", N is a natural number of from 1 to n, and CN denotes the concentration (kg/l) of the substance "n".

As apparent from the formula (2), the information on a plurality of optical active substance concentrations are included in the angle of rotation of the liquid obtained by measurement. Namely, the sum of the angle of rotation attributed to glucose and the angle of rotation attributed to albumin is included in the angle of rotation obtained for a urine.

From the fact that the specific rotatory power varies according to the wavelength of a light to be propagated, by using lights with a plurality of wavelengths, their respective specific rotatory powers are measured, thereby making it possible to determine the urine sugar value and the urine protein value from simultaneous equations comprising a plurality of the equations (2).

With this method, when one type of light source is used, if one of the urine sugar value and the urine protein value is known, it is possible to calculate the other value. However, when both the urine sugar value and the urine protein value are unknown, there occurs a problem that a plurality of light sources are required.

Further, with a conventional method for measuring the concentration of a solution, when the angle of rotation of a sample to be detected containing protein such as a urine or the like is measured, the sample has been required to be heated up to a relatively high temperature in the case where the sample is required to be opacified by heating.

The opacification phenomenon is affected by the pH of the sample to be detected. For example, the temperature at which opacification starts increases when the sample to be detected becomes alkaline. Namely, the opacification starting temperature increases with an increase in pH.

Therefore, in the case of a urine with a high pH, the urine is not opacified unless it is heated up to around 100° C. Since the urine can be heated up to only about 100° C. under an ordinary pressure, the urine may not be opacified when it is strongly alkaline. This is remarkable especially when the protein concentration is low.

Further, if the heating temperature exceeds about 80° C. for opacifying the urine with a high pH, a metal salt and the like suddenly tend to adhere to the walls of a sample cell, or the like. For this reason, there occurs a problem that the upkeep cost for removing them is increased. At the same time, for heating the urine up to around 100° C., i.e., the boiling point, it becomes necessary to reduce temperature distribution (nonuniformity) by heating to improve the temperature control accuracy so that the bumping or the like is avoided, resulting in more rigorous requirements for the apparatus performances. On the other hand, the heating rate is also required to be restricted for reducing the inconsistency in heating, resulting in a longer measurement time. Herein, it is noted that the "temperatuere distribution" means that the temperature of a solution to be detected is varied part by part. In other words, the temperature of the solution is not uniform and has a temperature variation part by part.

Further, when the sample to be detected is a urine, phosphate, carbonate, and the like have high concentrations, and hence the sample may become turbid by precipitation thereof from before heating. Upon heating such a urine, which has already been turbid from before heating, the opacification due to protein is further mixed therewith to affect the dynamic range of the urine protein concentration measurement.

It is therefore an object of the present invention to solve the foregoing problems. Namely, it is an object of the present invention to provide a method of urinalysis in which by heating and opacifying a sample to be detected (solution to be detected) containing protein such as a urine, projecting a light on the sample, and measuring the intensity of the light transmitted through the sample or the light scattered from the sample, the protein concentration of the sample can be evaluated with high precision.

BRIEF SUMMARY OF THE INVENTION

The present invention provides a method for measuring the concentration of a solution, comprising the steps of: (1) mixing an acid in a sample to be detected containing at least protein; (2) heating and opacifying the sample to be detected in which the acid has been mixed; (3) projecting a light on the opacified sample to be detected; (4) detecting a light transmitted through the sample to be detected and/or a light scattered from the sample to be detected out of the projected light; and (5) determining the protein concentration of the sample to be detected based on the intensity of a detected light.

In the aforesaid method, it is preferable that the step (2) and the step (3) are performed at the same time. Namely, it is preferable that, while heating the sample to be detected in which the acid has been mixed, a light is projected on the sample to be detected.

Herein, it is effective that, when the sample to be detected after being opacified contains a spontaneous optical active substance other than protein, a step of measuring the angle of rotation of the spontaneous optical active substance including protein in the sample to be detected is conducted before mixing the acid in the sample to be detected, and the concentration of the spontaneous optical active substance except for protein, and the concentration of protein in the sample to be detected are determined.

Further, it is also effective that the light transmitted through the sample to be detected and/or the light scattered from the sample to be detected are detected at two mutually different temperatures to determine the concentration of protein in the sample to be detected from the intensity ratio of the transmitted lights and/or the intensity ratio of the scattered lights.

It is preferable that the heating temperature is not less than the temperature at which the sample to be detected starts to be opacified, and not more than 80° C.

It is preferable that the two mutually different temperatures fall within a range of not less than the temperature at which the sample to be detected starts to be opacified, and not more than 80° C.

Further, in the aforesaid method for measuring the concentration of a solution, it is preferable that a calibration line (analytical line) with respect to the protein concentration is formed for every heating measurement pattern comprising a temperature at which heating of the sample to be detected is started, a heating rate, a heating completion temperature, a duration of time that the heating temperature is held constant, and a time point at which the transmitted light intensity and/or the scattered light intensity are measured.

Further in the aforesaid method for measuring the concentration of a solution of the present invention, it is preferable that the rate for heating the sample to be detected is set such that a maximum temperature portion in the sample to be detected due to the temperature distribution in heating is not more than the boiling point of the sample to be detected.

It is preferable that when the maximum temperature portion in the sample to be detected due to the temperature distribution in heating is not more than the boiling point of the sample to be detected, the rate for heating the sample to be detected is set at the maximum to reduce the measurement time.

It is effective that an aqueous acid solution is mixed in the sample to be detected to make the sample to be detected weakly acidic with a pH of less than 7.0 and, further, acidic with a pH of from 4.0 to 5.3. Herein, the acid to be mixed in the sample to be detected may also be either in the form of a liquid or a solid such as a powder.

It is effective that an aqueous solution of potassium hydrogenphthalate is mixed as an acid in the sample to be detected to make the pH of the sample to be detected within a range of from 4.0 to 4.3.

It is effective that an aqueous solution of acetic acid is mixed as an acid in the sample to be detected to make the pH of the sample to be detected within a range of from 4.9 to 5.3.

Further, it is effective that an aqueous solution of citric acid is mixed as an acid in the sample to be detected to make the pH of the sample to be detected within a range of from 4.7 to 5.2.

Still further, it is effective that an aqueous solution of ascorbic acid is mixed as an acid in the sample to be detected to make the pH of the sample to be detected within a range of from 4.3 to 4.8.

Further, it is preferable that when each of the acids is used in a solution form, the concentration of the acid solution is in the saturated state in the temperature range used in the aforesaid method for measuring the concentration of a solution.

Further, the present invention also relates to a solution concentration measuring apparatus for carrying out the foregoing method for measuring the concentration of a solution. Namely, the present invention relates to a solution concentration measuring apparatus, comprising: a light source for irradiating a sample to be detected with a light; a sample cell for holding the sample to be detected such that the light propagates through the sample to be detected; a photosensor for detecting the light transmitted through the sample to be detected, and/or a photosensor for detecting the scattered light arisen when the light propagates through the inside of the sample to be detected; a heater for heating the sample to be detected; a temperature sensor for detecting the temperature of the sample to be detected; a mixer for mixing a reagent in the sample to be detected; and a computer for controlling the heater and the mixer based on an output signal from the temperature sensor to analyze an output signal from the photosensor, wherein the sample to be detected is heated based on a prescribed heating measurement pattern, and the concentration of the sample to be detected is measured by using the output signal from the photosensor with the foregoing method for measuring the concentration of a solution.

Further, the present invention also relates to a solution concentration measuring apparatus, comprising: a monochromatic light source for projecting a substantially parallel light; a polarizer for transmitting only a polarization component in a specific direction out of the substantially parallel light; a sample cell for holding a sample to be detected such that the light transmitted through the polarizer transmits therethrough; a means for applying a magnetic field on the sample to be detected; a magnetic field control means for controlling the magnetic field; a magnetic field modulation means for vibration-modulating the magnetic field in controlling the magnetic field; an analyzer for transmitting only a polarization component in a specific direction out of the light transmitted through the sample to be detected; a photosensor for detecting the light transmitted through the analyzer; a lock-in amplifier for performing a phase sensitive detection on an output signal from the photosensor by using a vibration modulation signal from the magnetic field modulation means as a reference signal; a heater for heating the sample to be detected; a temperature sensor for detecting the temperature of the sample to be detected; a means for calculating the angle of rotation of the sample to be detected based on a magnetic field control signal from the magnetic field control means and an output signal from the lock-in amplifier, and converting it into the concentration of an optical active substance; a mixer for mixing an acid in the sample to be detected; and a computer for controlling the heater and the mixer based on an output signal from the temperature sensor to analyze an output signal from the photosensor, wherein the concentration of the sample to be detected is measured by the foregoing method for measuring the concentration of a solution, the method comprising the steps of: calculating the angle of rotation of the sample to be detected by controlling the magnetic field, and then mixing an acid in the sample to be detected by controlling the mixer: heating the sample to be detected based on a prescribed heating measurement pattern; and measuring the concentrations of protein and other spontaneous optical active substances than the protein in the sample to be detected by using an output signal from the photosensor.

In the solution concentration measuring apparatus, it is preferable that the means for applying a magnetic field on the sample to be detected is a solenoid coil wound around the sample cell, and it functions also as the heater by passing a current through the solenoid coil.

Further, the present invention also relates to a method of urinalysis using the foregoing method for measuring the concentration of a solution, when the sample to be detected is a urine, and the other spontaneous optical active substance than protein is glucose.

Further, the present invention also relates to a method of urinalysis using the foregoing method for measuring the concentration of a solution, when the sample to be detected is a urine, and the other optical active substance than protein is glucose.

Further, in the method for measuring the concentration of a solution, the solution concentration measuring apparatus, and the method of urinalysis in accordance with the present invention, a light with a wavelength of 500 nm or more is preferably used.

While the novel features of the invention are set forth particularly in the appended claims, the invention, both as to organization and content, will be better understood and appreciated, along with other objects and features thereof, from the following detailed description taken in conjunction with the drawings.

BRIEF DESCRIPTION OF THE SEVERAL VIEWS OF THE DRAWING

FIG. 3 is a graph showing the relation between a scattered light intensity and temperature;

FIG. 6 is a view showing a configuration of a solution concentration measuring apparatus used in Example 7 of the present invention;

FIG. 10 is a graph showing the relation between temperature and time.

DETAILED DESCRIPTION OF THE INVENTION

Figure 1:
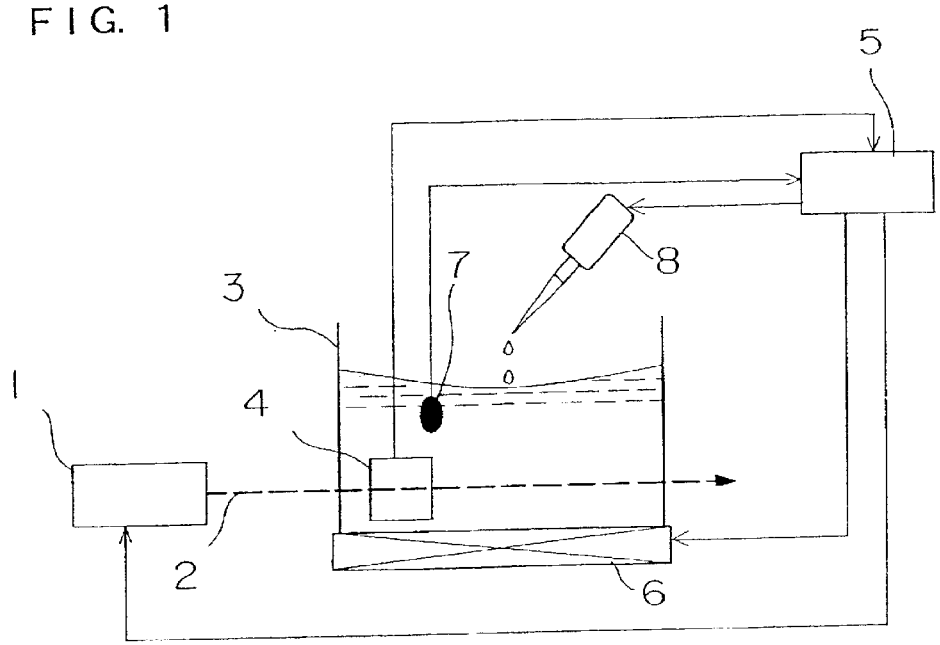
FIG. 1 is a view showing a configuration of a solution concentration measuring apparatus used in Example 1 of the present invention.
Figure 2:
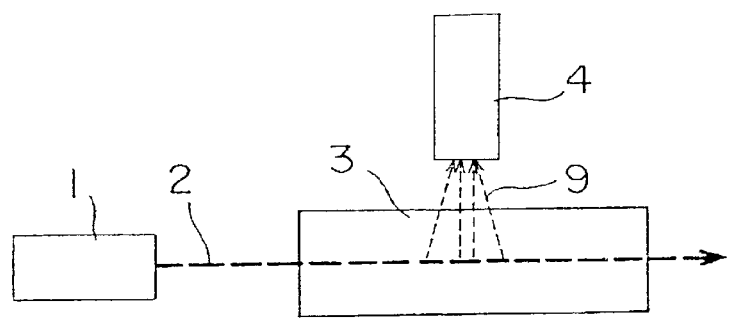
FIG. 2 is a top plan view schematically showing the solution concentration measuring apparatus shown in FIG. 1.

A method for measuring the concentration of a solution in accordance with the present invention mainly includes the steps of: (1) mixing an acid in a sample to be detected containing at least protein; (2) heating and opacifying the sample to be detected in which the acid has been mixed; (3) projecting a light on the opacified sample :to be detected; (4) detecting a light transmitted through the sample to be detected and/or a light scattered from the sample to be detected out of the projected light; and (5) determining the protein concentration of the sample to be detected based on the intensity of a detected light.

As described above, in a conventional method for measuring the concentration of a solution, when the angle of rotation of a sample to be detected containing protein such as a urine is measured, the sample to be detected has been required to be heated up to a relatively high temperature in the case where it is required to be opacified by heating.

In contrast, the present inventors have considered various problems and related matters on such a method for measuring the concentration of a solution, and they have wholeheartedly conducted experiments and study thereon. As a result, they have completed the present invention.

Namely, in the present invention, by mixing an acid in the sample to be detected, it is possible to reduce the heating temperature. That is, against the fact that the higher the pH of the sample to be detected is, the higher the temperature at which protein can be opacified is, the pH is reduced by mixing an acid therein, thereby making it possible to evaluate the protein concentration at a relatively low temperature with high precision.

Below, the method for measuring the concentration of a solution of the present invention will be described step by step.

First, in the step (1), an acid is mixed in the sample to be detected containing at least protein. At this step, stirring is preferably carried out so as to achieve homogeneous mixing. Further, this operation may be carried out in a so-called sample cell.

The sample to be detected in the present invention may be a liquid sample such as a solution containing at least protein, and for example, mention may be made of a urine, various culture solutions, and the like. Further, the sample to be detected may also contain a spontaneous optical active substance other than protein.

The acid usable in the present invention has no particular restriction so long as it does not obstruct the concentration measurement by decomposing protein, which is an object to be detected in the sample to be detected, or the like. Further, the acid usable may also be an acid in the form of a solid such as a powder. An acid solution, especially an aqueous acid solution is preferably used from the viewpoint that it can be efficiently mixed with especially a liquid sample to be detected.

As the aqueous acid solution, for example, various aqueous acid solutions such as an aqueous phosphoric acid solution and an aqueous hydrochloric acid solution can be used. Especially, for example, an aqueous potassium hydrogenphthalate solution, an aqueous acetic acid solution, or an aqueous ascorbic acid solution is preferably used from the viewpoints of ease of adjusting the pH of the sample to be detected, the low risk, and availability.

Further, the concentration of the aqueous acid solution is preferably in a saturated state within a temperature range used in the method for measuring the concentration of a solution of the present invention. The reason for this is that, if it is in such a saturated state, it is possible to restrict the reduction in the detection sensitivity due to the dilution effect to a minimum when it is added to the sample to be detected.

The acid may be mixed into the sample to be detected at any amount so long as it is capable of adjusting the pH of the sample to be detected within such a range that the sample to be detected containing protein can be opacified at a low temperature.

Herein, the pH of the sample to be detected in the method for measuring the concentration of a solution of the present invention is desirably less than 7.0. However, the pH of the sample to be detected after mixing of the acid is more preferably from 4.0 to 5.3 (weakly acidic) from the viewpoint of reducing as much as possible the temperature at which the sample to be detected is opacified by protein.

The concrete pH value may be selected according to the type of the aqueous solution of an acid used.

When an aqueous potassium hydrogenphthalate solution is mixed therein, the pH of the sample to be detected is preferably made from 4.0 to 4.3. Whereas, when an aqueous acetic acid solution is mixed therein, the pH of the sample to be detected is preferably made from 4.9 to 5.3.

Further, when an aqueous citric acid solution is mixed therein, the pH of the sample to be detected is preferably made from 4.7 to 5.2. When an aqueous ascorbic acid solution is mixed therein, the pH of the sample to be detected is preferably made from 4.3 to 4.8.

The fact that the preferable pH value thus varies with the type of the aqueous acid solution is attributable to the following fact. That is, the conjugate bases for respective acids differently affect the coagulation of protein.

It is noted that, the temperature of the sample to be detected, or the aqueous acid solution is desirably the temperature in the normal house (room temperature), i.e., from about 0 to 40° C. Further, there is no particular restriction on the amount of protein contained in the sample to be detected.

Then, in the step (2), the sample to be detected in which the acid has been mixed is heated and opacified.

Any temperature, to which the sample to be detected is heated, is acceptable so long as it is capable of opacifying the sample to be detected. However, the heating temperature is preferably 80° C. or less from the viewpoint of preventing especially a metal salt or the like, contained in a urine from precipitating and adhering to the walls of the sample cell, and the like.

Therefore, it is preferable that the mixing amount of the acid is appropriately changed and adjusted in accordance with the composition and the type of the sample to be detected, and the like so that the sample to be detected is opacified at a temperature of 80° C. or less.

Further, the rate for heating the sample to be detected is preferably set so that the maximum temperature portion in the sample to be detected occurred due to the temperature distribution in heating is not more than the boiling point of the sample to be detected. Further, it is preferable that, when the maximum temperature portion in the sample to be detected occurred due to the temperature distribution in heating is not more than the boiling point of the sample to be detected, the rate at which the sample to be detected is heated is preferably set at the maximum to reduce the measurement time.

The reason for this is as follows. That is, if the temperature distribution occurs, a temperature of the sample to be detected reaches partially the boiling point. Accordingly, the optical path is obstructed by vapor bubbles arisen, and hence it becomes impossible to measure the angle of rotation. It is noted that there is no particular restriction on the lower limit of the heating rate.

Further, as the step (3), a light is projected on the opacified sample to be detected.

The irradiation light (to be projected) may be a substantially parallel light, a convergent light, or the like, and has no particular restriction.

The intensity of the projected light has no particular restriction so long as it falls within such a range that the light transmitted through the sample to be detected, and the light scattered from the sample to be detected can be effectively detected. However, the light preferably has a wavelength of 500 nm or more.

The specific rotatory power of the optical active substance increases with a decrease in wavelength until the anomalous dispersion occurs due to the optical rotatory dispersion as shown in Table 1 described above. Therefore, a light with a shorter wavelength is desirably used for ensuring a high precision evaluation. However, in general, a light with a wavelength of 500 nm or less undergoes high absorption by a urine component such as urochrome, and hence a light with a wavelength of 500 nm or more is desirably used.

Then, in the step (4), the light transmitted through the sample to be detected and/or the light scattered from the sample to be detected is detected out of the projected light. In the step (5), the protein concentration of the sample to be detected is determined based on the intensity of the detected light.

The detection of the transmitted light and the scattered light, and the determination of the protein concentration based on the intensity of the detected light may be carried out in accordance with the conventionally known method and conditions.

Herein, the protein concentration may also be determined in the following manner. Namely, while heating the sample to be detected in which the acid has been mixed, a light is projected on the sample to be detected to measure the transmitted light and/or the scattered light to determine the protein concentration from the amount of changes in intensity of the light with respect to the sample to be detected. That is, the steps (2) and (3) are preferably performed simultaneously. Further, it is also possible to perform the steps (2) to (5) simultaneously.

The measurement of the intensity of the transmitted light or the scattered light is not required to be carried out continuously. It is possible to determine the protein concentration by measuring the intensities of the transmitted light or the scattered light at two different temperatures. Further, it is also possible to determine the protein concentration by using the ratio of the intensities of the transmitted light or the scattered light obtained at such two points. For example, the measurements are carried out at two points within a range of from 60 to 80° C., and the protein concentration can be determined from the ratio of intensities of the transmitted light or the scattered light at these two points.

As described above, the opacification of the sample containing protein proceeds with an increase in temperature. Then, by detecting the transmitted light or the scattered light at the same time while heating the sample, it is possible to determine (evaluate) the protein concentration of the sample from the amount of changes with respect to the temperatures. For example, the protein concentration is calculated from the ratio of the scattered light intensity at 70° C. and the scattered light intensity at 75° C. Consequently, it is possible to reduce the influences of scattering by other substances than protein, and the like.

Further, when the sample to be detected contains a spontaneous optical active substance other than protein (ex., glucose, albumin, or the like), there is preferably included a step of measuring the angle of rotation of the spontaneous optical active substance including protein in the sample to be detected before mixing the acid in the sample to be detected. Consequently, the concentration of only protein can be determined through the foregoing steps (1) to (5), and the concentration of the spontaneous optical active substance except for protein in the sample to be detected can also be determined.

By performing this pre-step, it is possible to evaluate the urine sugar value as well as the urine protein value with high precision especially in a urinalysis. More concretely, the urine protein value is calculated by comparing the transmitted light amount or the scattered light amount with a calibration line, and the urine protein value thus obtained and the angle of rotation of the urine are substituted in the formula (2) to yield the urine sugar value.

In the present invention, it is also effective that a calibration line with respect to the protein concentration is formed for every heating measurement pattern comprising the temperature at which heating of the sample to be detected is started, the heating rate, the heating completion temperature, the duration of time that the heating temperature is held constant, and the time points at which the transmitted light intensity and the scattered light intensity are measured.

It is possible to determine or evaluate the protein concentration in the sample to be detected with high efficiency in the foregoing manner in accordance with the method of the present invention.

Then, the present invention also relates to a solution concentration measuring apparatus for carrying out the foregoing method for measuring the concentration of a solution.

The method for measuring the concentration of a solution of the present invention can be carried out by using the conventionally known apparatus, examples of which include the following one.

That is, there can be used a solution concentration measuring apparatus, comprising: a light source for irradiating a sample to be detected with a light; a sample cell for holding the sample to be detected such that the light propagates through the sample to be detected; a photosensor for detecting the light transmitted through the sample to be detected, and/or a photosensor for detecting the scattered light arisen when the light propagates through the inside of the sample to be detected; a heater for heating the sample to be detected; a temperature sensor for detecting the temperature of the sample to be detected; a mixer for mixing a reagent in the sample to be detected; and a computer for controlling the heater and the mixer based on an output signal from the temperature sensor to analyze an output signal from the photosensor.

With this apparatus, it is possible to measure the concentration of the sample to be detected by heating the sample to be detected based on a prescribed heating measurement pattern, and using an output signal from the photosensor in accordance with the method for measuring the concentration of a solution.

Further, there can also be used a solution concentration measuring apparatus, comprising: a monochromatic light source for projecting a substantially parallel light; a polarizer for transmitting only a polarization component in a specific direction out of the substantially parallel light; a sample cell for holding a sample to be detected such that the light transmitted through the polarizer transmits therethrough; a means for applying a magnetic field on the sample to be detected; a magnetic field control means for controlling the magnetic field; a magnetic field modulation means for vibration-modulating the magnetic field in controlling the magnetic field; an analyzer for transmitting only a polarization component in a specific direction out of the light transmitted through the sample to be detected; a photosensor for detecting the light transmitted through the analyzer; a lock-in amplifier for performing a phase sensitive detection on an output signal from the photosensor by using a vibration modulation signal from the magnetic field modulation means as a reference signal; a heater for heating the sample to be detected; a temperature sensor for detecting the temperature of the sample to be detected; a means for calculating the angle of rotation of the sample to be detected based on a magnetic field control signal from the magnetic field control means and an output signal from the lock-in amplifier, and converting it into the concentration of an optical active substance; a mixer for mixing an acid in the sample to be detected; and a computer for controlling the heater and the mixer based on an output signal from the temperature sensor to analyze an output signal from the photosensor.

With this apparatus, the angle of rotation of the sample to be detected is calculated by controlling the magnetic field, and then an acid is mixed in the sample to be detected by controlling the mixer to heat the sample to be detected based on a prescribed heating measurement pattern, and thus, the concentrations of protein and a spontaneous optical active substance other than the protein in the sample to be detected can be measured by using an output signal from the photosensor.

The means for applying a magnetic field has no particular restriction so long as it is an apparatus capable of applying a magnetic field on the sample to be detected, and examples thereof include a coil, a permanent magnet, and the like.

Further, as the magnetic field control means, for example, a current driver for injecting a current in the coil, a stage for controlling the position of a permanent magnet, or the like can be used. As the magnetic field modulation means, for example, a signal generator for modulating the injection current from the current driver or the position of the stage, or the like can be used.

Especially, it is preferable that the means for applying a magnetic field on the sample to be detected is a solenoid coil wound around the sample cell, and it functions as the heater by passing a current through the solenoid coil. The reason for this is that this configuration can simplify the structure of the apparatus.

Further, a computer or the like can be used as the means for calculating the angle of rotation of the sample to be detected based on the magnetic field control signal from the magnetic field control means and the output signal from the lock-in amplifier, and converting it into the concentration of an optical active substance.

As described above, since the method for measuring the concentration of a specific component of the present invention is capable of evaluating the protein concentration of the sample to be detected with high precision, it is useful especially for a urinalysis. Namely, according to the present invention, it becomes possible to measure the urine protein value with high precision without requiring consumable items.

Herein, a description will be given to the urine which is a typical object for the measuring method of the present invention.

A healthy adult generally excretes a urine in an amount of from 1000 to 1500 ml per day. The total solid content thereof is from 50 to 70 g. Inorganic matters, which mainly composed of sodium chloride and potassium chloride, account for about 25 g out of the solid content, and they are mostly dissolved in the urine in an ionized state. Further, organic matters such as urea and uric acid, phosphoric acid, trace amount of sugar, i.e., glucose, and protein are also contained therein. The main component of protein in the urine is albumin, but globulin and the like are also present therein.

In general, 0.13 to 0.5 g of glucose is contained in the excreted urine per day. The concentration of glucose in the urine, i.e., the urine sugar value can be roughly estimated from the amount of the glucose and the amount of the urine, and an average urine sugar value is about 50 mg/dl or less. However, for a diabetic, the urine sugar value is several hundreds mg/dl, and may sometimes reach several thousands mg/dl. Namely, it increases relative to a normal value by one to two orders of magnitude.

On the other hand, the amount of albumin is generally further less than the amount of glucose, and albumin is excreted in an amount of from 3 to 60 mg with a urine per day. Roughly estimated from the amount of the albumin and the amount of the urine, the albumin concentration in the urine, i.e., the urine protein value is generally about 6 mg/dl or less. However, the urine protein value of a patient having renal diseases is 100 mg/dl or more, and it may become not less than 10 times as high as the normal value.

The urine which is one of the foregoing samples to be detected is opacified upon heating up to from 60 to 100° C. This is attributable to the fact that albumin which is protein contained in the urine coagulates into a macro colloid. Even if the urine is heated to such a degree of temperature, other components such as glucose do not change. Therefore, the intensity of the light transmitted through the urine or the light scattered from the urine out of the light projected on the opacified urine depends upon the urine protein value.

Therefore, by projecting a light on the opacified urine to measure the intensity of the scattered light or the transmitted light, and comparing it with a previously formed calibration line (i.e., the relational equation between the concentration of an aqueous albumin solution and the intensity of the scattered light or the transmitted light), it is possible to evaluate the albumin concentration, i.e., the protein value of the urine.

However, this opacification phenomenon is affected by the pH of the sample to be detected. For example, the opacification starting temperature increases with an increase in pH. Therefore, for an alkaline urine with a high pH, opacification does not occur unless the urine is heated up to around 100° C.

Then, when the following examples were carried out in accordance with the present invention, it was possible to decrease the opacification starting temperature by mixing an acid in the urine and thereby reducing the pH. Consequently, it was also possible to opacify a highly alkaline urine at the same time. Further, by setting the heating temperature at about 80° C. or less with the mixing of an acid, it was possible to prevent a metal salt or the like from adhering to the wall of the sample cell, or the like. Further, by setting the heating temperature at about 80° C. or less, i.e., a temperature sufficiently lower than the boiling point, it was possible to reduce the temperature distribution and thereby to relax the requirements for the apparatus performances such as the improvement of the temperature control precision.

Further, by reducing the pH with the mixing of an acid, it was possible to dissolve precipitated crystals such as phosphate and carbonate. Consequently, it was possible to clear the urine, which had been opacified by precipitation of these salts. Therefore, it was possible to ensure the dynamic range of the urine protein concentration measurement for the urine which had been opacified from before heating.

Still further, by measuring the angle of rotation of the urine as described above, it was possible to obtain information on the optical active substances, i.e., glucose and albumin, contained in the urine. Then, by measuring the angle of rotation of the urine in advance, and then opacifying the urine with heating to measure the degree of opacity as described above, it was possible to evaluate the urine sugar value with high precision in addition thereto. Consequently, it was possible to implement a method of urinalysis which requires no consumable items, and is easy to maintain and control.

Below, the present invention will be described by way of examples, which should not be construed as limiting the scope of the present invention.

EXAMPLE 1

The configuration of a measuring apparatus used in this example is shown in FIG. 1. In this example, a sample to be detected containing protein such as a urine was heated, and further, while measuring the temperature thereof, the intensity of the scattered light arisen in the sample to be detected was measured. A projector module serving as a light source 1 included an optical system using a semiconductor laser as a light source, and a driving circuit of the semiconductor laser. The projector module projected a substantially parallel light 2 having a wavelength of 670 nm, and an intensity of 5 mW on a sample cell 3. The sample cell 3 had the shape of a rectangular parallelepiped open upwards, and was made of glass, and a sample to be detected was held in the inside thereof. Then, the substantially parallel light 2 was propagated through the inside of the sample to be detected. The sample cell 3 had a substantial optical path length of 50 mm, and a rate capacity of 10 ml.

The scattered light arisen when the substantially parallel light 2 propagated through the sample to be detected was detected by a photosensor 4. A computer 5 had the light source 1, which was a projector module, and analyzed an output signal from the photosensor 4. A heater 6 heated the sample to be detected together with the sample cell 3, and it was controlled by the computer 5. The temperature of the sample to be detected was detected by a temperature sensor 7, and the detected result was monitored by the computer 5. A pipette 8 for mixing an acid in the sample to be detected was also controlled by the computer 5.

The following sample to be detected (urine solution) was prepared by using a urine having a pH of 6.1, of which the protein concentration had been previously judged as being not more than 1 mg/dl by a dye coupling method (pyrogallol red/molybdenum complex coloring method).

First, 30 mg of albumin was weighed to be charged in a 1-dl measuring flask, and the urine was charged therein to prepare a urine solution with a volume of 1 dl. The protein concentration of the urine solution was about 30 mg/dl. Expressing it more precisely, the protein concentration of the urine solution was from 30 to 31 mg/dl. Whereas, the pH of the urine solution was 6.0.

Similarly, four types of urines with different pHs, of which the protein concentration had been previously judged as being not more than 1 mg/dl were used as solvents to prepare urine solutions having a concentration of 30 mg/dl. Their respective pHs were 5.0, 6.6, 7.3, and 8.5.

The five types of urines with different pHs, and a protein concentration of about 30 mg/dl were respectively introduced into the sample cell 3, and heated from 35° C. to around 93° C. at a heating rate of 20° C./min, and the temperature was fixed around 93° C. for 2 minutes.

The heating pattern at this step is shown by a solid line in FIG. 10. In FIG. 10, the abscissa indicates the elapsed time, while the ordinate indicates the temperature. Herein, there occurs a problem as follows. If the heating rate exceeds 20° C./min, the temperature distribution at the time of heating is increased, and a part of the sample reaches the boiling point. Accordingly, the optical path is obstructed by a vapor bubble arisen, and hence it becomes impossible to carry out the measurement. Therefore, when the sample is heated up to 93° C., the upper limit of the heating rate is 20° C./min.

FIG. 3 shows the variations in output signal (voltage) from the photosensor 4, that is, the variations in scattered light intensity. Herein, the temperature of the sample is plotted as abscissa, while the output signal voltage from the photosensor 4 for the scattered light intensity as ordinate. The variations in scattered light intensity with respect to the samples to be detected with pHs of 5.0, 6.0, 6.6, 7.3, and 8.5 are indicated with marks ○, □, ◇, X, and ●, respectively.

FIG. 3 indicates that, the lower the pH is, the lower the opacification starting temperature is. For example, the sample to be detected with a pH of 5.0, indicated with the mark ○ increases in scattered light intensity, that is, starts to show its opacification from around 75° C. However, the opacification is not observed until up to around 93° C. for the sample to be detected with a pH of 7.3, indicated with the mark X. Further, there is observed no opacification, that is, the scattered light intensity does not increase for the sample to be detected with a pH of 8.5, indicated with the mark ●.

Further, as apparent from FIG. 3, under the conditions shown in this example, a highly alkaline urine with a pH of 8.5 or more cannot be opacified, so that the protein concentration cannot be measured. Further, if it is assumed that the sample is heated only up to around 80° C., under the conditions shown in this example, the sample to be detected, with a pH of about 6.6 or more cannot be opacified, so that the protein concentration cannot be measured.

Then, 10 ml of the sample to be detected, with a protein concentration of about 30 mg/dl, and a pH of 8.5 (the same sample to be detected as that indicated with the mark ● in the foregoing paragraph) was charged into the sample cell 3. About 0.5 ml of an aqueous solution of potassium hydrogenphthalate with a molar concentration of 0.5 M (mol/L) was mixed therein by the pipette 8. At this step, the pH of the sample to be detected was 4.3.

The variations in output signal from the photosensor 4 with respect to the sample to be detected are indicated with a bold solid line of FIG. 3. The bold solid line in FIG. 3 indicates that opacification starts from about 60° C. From the scattered light intensity finally achieved at this step, it is indicated that the reduction in degree of opacity due to dilution is negligible for such a degree of the volume of the aqueous solution of potassium hydrogenphthalate mixed.

Further, similarly, 0.5 ml of 0.5 M aqueous solution of potassium hydrogenphthalate described above was mixed into 10 ml of each of four types of the samples to be detected with an albumin concentration of about 30 mg/dl and pHs of 5.0, 6.0, 6.6, and 7.3. At this step, the pHs of the samples to be detected exhibited 4.0, 4.1, 4.1, and 4.2, respectively. Then, as the output signal from the photosensor 4 with respect to respective samples to be detected, the same values as those on the bold solid line of FIG. 3 were obtained. Namely, there was obtained the same result as with the case where about 0.5 ml of aqueous solution of potassium hydrogenphthalate with a molar concentration of 0.5 M (mol/L) was mixed into 10 ml of the sample to be detected having a pH of 8.5.

Thus, by mixing an acid such as the aqueous solution of potassium hydrogenphthalate into the sample to be detected to set the pH at from 4.0 to 4.3, it was possible to equalize the opacification starting temperatures of the samples to be detected originally having different pHs. At the same time, it was also possible to reduce the opacification starting temperature down to around 60° C. Further, it was also possible to equalize the scattered light intensities at the completion of heating.

Then, the measurements were carried out on the urines whose protein concentration had been measured to be 12, 63, and 99 mg/dl by a dye coupling method in the following manner. Incidentally, the urines with protein concentrations of 12, 63, and 99 mg/dl had pHs of 6.6, 5.2, and 5.7, respectively. Further, measurements were also carried out on the urine used above, judged as having a protein concentration of not more than 1 mg/dl, and having a pH of 6.1, and further the urine having a protein concentration of about 30 mg/dl, and a pH of 6.0, prepared by using it. Namely, measurements were carried out on a total of 5 types of samples to be detected.

The sample to be detected was introduced in an amount of 10 ml into the sample cell 3, and about 0.5 ml of an aqueous solution of potassium hydrogenphthalate with a molar concentration of 0.5 M (mol/L) was mixed therein. At this step, the pH of every sample to be detected was 4.1. The samples to be detected were heated from 35° C. to 80° C. at a heating rate of 20° C./min. This heating pattern is indicated with a bold solid line of FIG. 10. The scattered light intensity at this time, i.e., the output signal from the photosensor 4 is as shown with the bold solid line of FIG. 3, indicating that the opacification proceeded from 80° C. or less.

Figure 4:
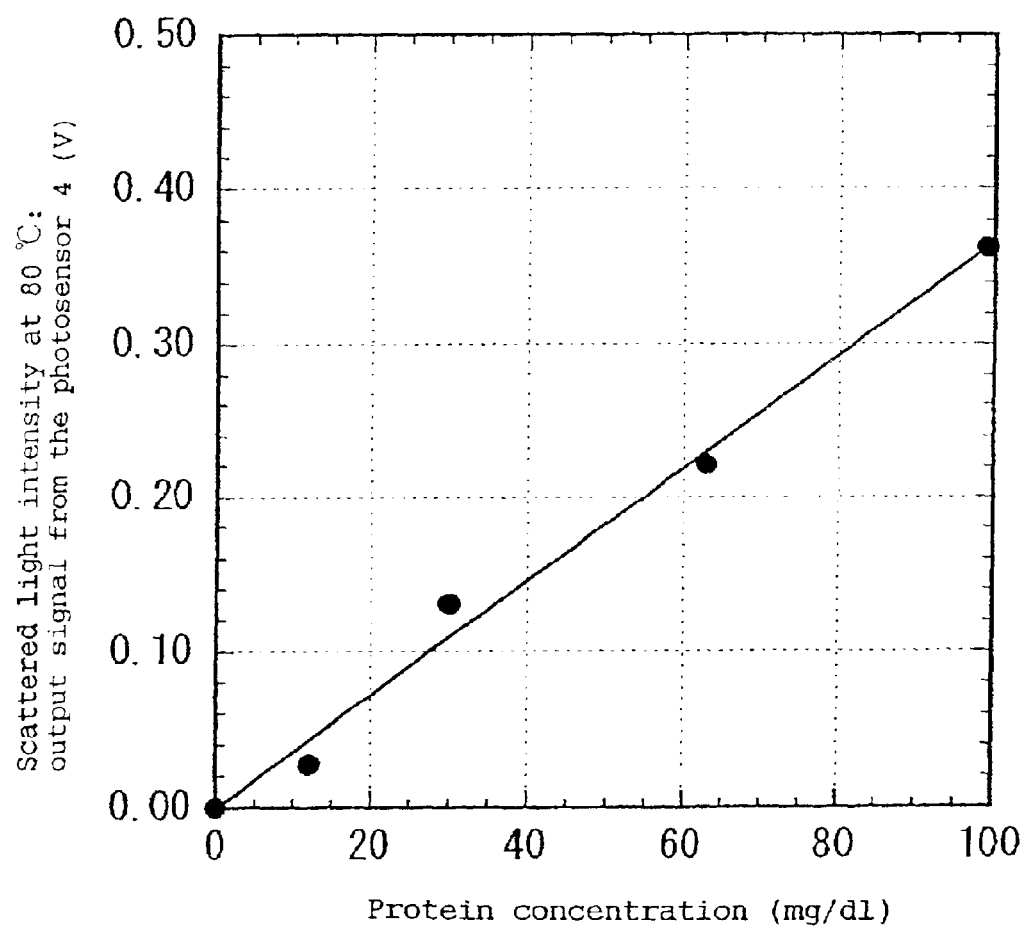
FIG. 4 is a graph showing the relation between a scattered light intensity and a protein concentration.

Then, FIG. 4 shows the relation between the protein concentration of the sample to be detected, and the scattered light intensity, i.e., the output signal from the photosensor 4 when the temperature has reached 80° C. The ordinate denotes the scattered light intensity, while the abscissa denotes the protein concentration of the sample to be detected. The heating measurement pattern indicated with the bold solid line of FIG. 10 was used in forming the graph of FIG. 4. Namely, the scattered light intensity was measured at the point of time, at which the temperature had reached 80° C. indicated with a measurement point 1. In FIG. 4, a regression line obtained by using five points is indicated with a solid line.

From FIG. 4, it has been confirmed that the scattered light intensity when the temperature has reached 80° C. is proportional to the protein concentration without being affected by the original pH (the pH before the mixing of the acid) of the sample to be detected. It is possible to measure the protein concentration by using the regression line indicated with the solid line as a calibration line.

As described above, as in this example, by mixing an acid in each of the samples to be detected, acidifying it to reduce the variations in pH, and thereby substantially equalizing the opacification starting temperatures, it is possible to measure the protein concentration without being affected by the original pH of each sample to be detected. Consequently, the opacification starting temperature can also be reduced down to not more than 80° C., so that adhesion of dirt due to a metal salt or the like onto the sample cell can also be reduced. Further, it is also possible to measure the protein concentration of a highly alkaline urine with a pH of about 8.5.

Incidentally, when the urine is heated up to only not more than 80° C., it is also possible to set the heating rate at 20° C./min or more, but in this case, it is necessary to form another calibration line. Likewise, although the heating starting temperature was 35° C. in this example, even when heating is started from other temperature than this temperature, it is also necessary to form another calibration line.

Further, in this example, there was shown the example in which the sample to be detected was heated in the sample cell 3. However, the following procedure is also acceptable. The sample to be detected heated from 35° C. to 80° C. under the same condition, i.e., at a heating rate of 20° C./min in another container is charged into the sample cell 3. Then, the output signal from the photosensor 4 is read to determine the protein concentration from the calibration line of FIG. 4. However, an error tends to be increased because a difference in time and a difference in temperature between the time point when the temperature has reached 80° C. and the time point of measurement are likely to occur.

Incidentally, in this example, there was shown the example in which about 0.5 ml of an aqueous solution of potassium hydrogenphthalate with a molar concentration of 0.5 M (mol/L) was mixed into 10 ml of each sample to be detected to set the pH at from 4.0 to 4.3. However, by mixing the aqueous solution of potassium hydrogenphthalate into each sample to be detected even in other concentrations and mixing ratios of the aqueous solution of potassium hydrogenphthalate to set the pH at from 4.0 to 4.5, it was possible to substantially equalize the opacification starting temperatures, and at the same time to set the temperature at not more than 80° C. For example, even by mixing 5 ml of 0.1 M aqueous solution of potassium hydrogenphthalate in 10 ml of the sample to be detected, it was possible to set the pH at from 4.0 to 4.3. Thus, by forming a calibration line with the use of this mixing ratio, it was possible to measure the protein concentration. However, when a low-concentration aqueous solution of potassium hydrogenphthalate is mixed therein, the degree of dilution is increased, so that the slope of the calibration line is decreased. Accordingly, the sensitivity may be reduced. Therefore, when the sensitivity is required to be improved, a high-concentration acid solution is desirably mixed therein so long as precipitation does not occur at a temperature used.

EXAMPLE 2

In this example, the same apparatus (shown in FIG. 1) as in Example 1 was used. Further, the same samples to be detected as in Example 1 were also used to carry out the measurements.

First, five types of samples to be detected with a protein concentration of about 30 mg/dl, and with respective pHs of 5.0, 6.0, 6.6, 7.3, and 8.5 were prepared in the same manner as in Example 1. Into 10 ml of each of the samples to be detected, was mixed 2 $\mu$l of acetic acid with a concentration of 96% or more. Consequently, the pHs of the samples to be detected become, 4.9, 5.1, 5.1, 5.2, and 5.3, respectively. These samples were heated in the same manner as in Example 1, and the values of the output signal from the photosensor 4 with respect to the samples to be detected were plotted in FIG. 3, resulting in a line having the form of the bold solid line of FIG. 3 all translated toward the higher temperature side by about 5° C. Namely, the opacification was started from about 65° C.

Thus, by mixing an acid such as acetic acid into each sample to be detected to set the pH at from 4.9 to 5.3, it was possible to equalize the opacification starting temperatures of the samples to be detected originally having different pHs. At the same time, it was possible to reduce the opacification starting temperature down to around 65° C. Further, it was also possible to equalize the scattered light intensities at the completion of heating.

Then, in the same manner as in Example 1, into 10 ml of each of urines with a protein concentration of 12, 63, or 99 mg/dl and with respective PHs of 6.6, 5.2, and 5.7, and a urine with a protein concentration of about 30 mg/dl and a pH of 6.0 prepared by adding albumin thereto, was mixed 2 $\mu$l of acetic acid with a concentration of 96% or more. At this step, the pH of every sample to be detected become 5.1. The samples to be detected were heated from 35° C. to 80° C. at a heating rate of 20° C./min in the same manner as in Example 1. The scattered light intensity at this time, i.e., the output signal from the photosensor 4 was as shown with the bold solid line of FIG. 3, indicating that the opacification proceeded from 80° C. or less. The result was shown by forming a regression line indicating the relation between the output signal from the photosensor 4 when the temperature has reached 80° C., and the protein concentration as with Example 1. It was possible to measure the protein concentration by using the regression line as a calibration line.

As in this example, by mixing acetic acid in each of the samples to be detected to set the pH at from 4.9 to 5.3, and thereby substantially equalizing the opacification starting temperatures, it is possible to measure the protein concentration without being affected by the original pH of the sample to be detected.

Incidentally, in this example, there was shown the example in which into 10 ml of each sample to be detected, was mixed 2 µl of acetic acid with a concentration of 96% or more to set the pH at from 4.9 to 5.3. However, by setting the pH at from 4.9 to 5.5 even in other mixing ratios, the same effects can be obtained. Further, by setting the pH at from 4.9 to 5.5 even by using an aqueous solution of acetic acid with an appropriate concentration, the same effect can also be obtained.

EXAMPLE 3

In this example, the same apparatus (shown in FIG. 1) as in Example 1 was used. Further, the same samples to be detected as in Example 1 were also used to carry out the measurements.

First, five types of samples to be detected with a protein concentration of about 30 mg/dl and with respective pHs of 5.0, 6.0, 6.6, 7.3, and 8.5 were prepared in the same manner as in Example 1. Into 10 ml of each of the samples to be detected, was mixed 5 µl of an aqueous solution of citric acid with a concentration of 1.56 M. Consequently, the pHs of the samples to be detected become 4.7, 4.8, 4.8, 5.0, and 5.2, respectively. These samples to be detected were heated in the same manner as in Example 1, and the values of the output signal from the photosensor 4 with respect to the samples to be detected were plotted in FIG. 3, resulting in a line having the form of the bold solid line of FIG. 3 all translated toward the higher temperature side by about 10° C. Namely, the opacification was started from about 70° C.

Thus, by mixing an acid (for example, an aqueous solution of citric acid) into each of the samples to be detected to set the pH at from 4.7 to 5.2, it was possible to equalize the opacification starting temperatures of the samples to be detected originally having different pHs. At the same time, it was possible to reduce the opacification starting temperature down to around 70° C. Further, it was also possible to equalize the scattered light intensities at the completion of heating.

Then, in the same manner as in Example 1, there were prepared urines with a protein concentration of 12, 63, or 99 mg/dl and with respective PHs of 6.6, 5.2, and 5.7, and a urine with a protein concentration of about 30 mg/dl and a pH of 6.0 prepared by adding albumin thereto. Into 10 ml of each of the urines, was mixed 5 µl of an aqueous solution of citric acid with a concentration of 1.56 M. At this step, the pH of every sample to be detected become 4.8. The samples to be detected were heated from 35° C. to 80° C. at a heating rate of 20° C./min in the same manner as in Example 1. The scattered light intensity at this time, i.e., the output signal from the photosensor 4 was plotted in FIG. 3, resulting in the same line as the bold solid line of FIG. 3. This indicates that the opacification proceeded from 80° C. or less. Based on the result, a regression line indicating the relation between the output signal from the photosensor 4 when the temperature has reached 80° C., and the protein concentration was formed as with Example 1. It was possible to measure the protein concentration by using the regression line as a calibration line.

As described above, as in this example, by mixing citric acid in each sample to be detected to set the pH at from 4.7 to 5.2, and thereby substantially equalizing the opacification starting temperatures, it was possible to measure the protein concentration without being affected by the original pH of each sample to be detected.

Incidentally, in this example, there was shown the example in which into 10 ml of each sample to be detected, was mixed 5 µl of an aqueous solution of citric acid with a concentration of 1.56 M to set the pH at from 4.7 to 5.2. However, by setting the pH at from 4.7 to 5.2 even in other concentrations and mixing ratios, the same effects can be obtained. However, when a low-concentration aqueous solution of citric acid is mixed therein, the degree of dilution is increased, so that the slope of the calibration line is decreased. Accordingly, the sensitivity may be reduced. Therefore, when the sensitivity is required to be improved, a high-concentration acid solution is desirably mixed therein so long as precipitation does not occur at a temperature used. For example, assuming that it is used at not less than 30° C., it is possible to set the concentration up to as high as about 3.0 M for citric acid.

EXAMPLE 4

In this example, the same apparatus (shown in FIG. 1) as in Example 1 was used. Further, the same samples to be detected as in Example 1 were also used to carry out the measurements.

First, five types of samples to be detected with a protein concentration of about 30 mg/dl and with respective pHs of 5.0, 6.0, 6.6, 7.3, and 8.5 were prepared in the same manner as in Example 1. Into 10 ml of each of the samples to be detected, was mixed 5 µl of an aqueous solution of ascorbic acid with a concentration of 1.7 M. Consequently, the pHs of the samples to be detected become 4.3, 4.4, 4.4, 4.6, and 4.8, respectively. These samples were heated in the same manner as in Example 1, when the values of the output signal from the photosensor 4 with respect to the samples to be detected were plotted in FIG. 3, resulting in a line having the form of the bold solid line of FIG. 3 all translated toward the higher temperature side by about 10° C. Namely, the opacification was started from about 70° C.

Thus, by mixing an acid, for example, an aqueous solution of ascorbic acid into each sample to be detected to set the pH at from 4.3 to 4.8, it was possible to equalize the opacification starting temperatures of the samples to be detected originally having different pHs. At the same time, it was possible to reduce the opacification starting temperature down to around 70° C. Further, it was also possible to equalize the scattered light intensities at the completion of heating.

Then, in the same manner as in Example 1, there were prepared urines with a protein concentration of 12, 63, or 99 mg/dl and with respective PHs of 6.6, 5.2, and 5.7, and a urine with a protein concentration of about 30 mg/dl and a pH of 6.0, prepared by adding albumin thereto. Into 10 ml of each of the urines, was mixed 5 µl of an aqueous solution of ascorbic acid with a concentration of 1.7 M. At this step, the pH of every sample to be detected become 4.4. The samples to be detected were heated from 35° C. to 80° C. at a heating rate of 20° C./min in the same manner as in Example 1. The scattered light intensity at this time, i.e., the output signal from the photosensor 4 was plotted in FIG. 3, resulting in the line as indicated with the bold solid line of FIG. 3. This indicates that the opacification proceeded from 80° C. or less. Based on the result, a regression line indicating the relation between the output signal from the photosensor 4 when the temperature had reached 80° C., and the protein concentration was formed as with Example 1. It was possible to measure the protein concentration by using the regression line as a calibration line.

As in this example, by mixing ascorbic acid in each sample to be detected to set the pH at from 4.3 to 4.8, and thereby substantially equalizing the opacification starting temperatures, it was possible to measure the protein concentration without being affected by the original pH of each sample to be detected.

Incidentally, in this example, there was shown the example in which into 10 ml of each sample to be detected, was mixed 10 μl of an aqueous solution of ascorbic acid with a concentration of 1.7 M to set the pH at from 4.3 to 4.8. However, by setting the pH at from 4.3 to 4.8 even in other concentrations and mixing ratios, the same effects can also be obtained

EXAMPLE 5

In this example, the measurement was carried out on a urine, which had been opacified by precipitation of phosphate by using the same apparatus (shown in FIG. 1) as in Example 1.

The protein concentration of the urine herein used was measured by a dye coupling method, and as a result, it was found to be 30 mg/dl. The pH was 6.6. When the urine was charged into the sample cell 3 to operate the projector module 1, the output signal from the photosensor 4 showed 0.4 V even prior to heating (35° C.). This signal intensity corresponds to the degree of opacity exhibited when the urine with a protein concentration of 100 mg/dl or more was heated up to about 80° C. Thus, the degree of opacity of the urine, in which phosphate has been precipitated, is equal to or greater than the degree of the urine opacified due to coagulation of protein by heating.

Even when the urine opacified by precipitation of phosphate is heated, the protein coagulates to increase the degree of opacity, so that the output signal from the photosensor 4 is also increased. At this time, the output signal may be saturated in relation to the dynamic range of the photosensor 4. Further, when the degree of precipitation of the phosphate is high, the output signal from the photosensor 4 is saturated from before heating.

Herein, 10 ml of the urine opacified by precipitation of phosphate was introduced into the sample cell 3, and about 0.5 ml of an aqueous solution of potassium hydrogenphthalate with a molar concentration of 0.5 M (mol/L) was mixed therein. Consequently, the phosphate was dissolved to make the urine transparent. At this time, the pH of the urine was 4.1, and the output signal from the photosensor 4 before heating was reduced down to about 0.005 V.

Then, the urine was heated from 35° C. to 80° C. at a heating rate of 20° C./min in the same manner as in Example 1. The scattered light intensity at this step, i.e., the output signal from the photosensor 4 was plotted in FIG. 3, resulting in a precisely identical line with the bold solid line of FIG. 3 until 80° C. Namely, the opacification started from around 60° C., and the output signal from the photosensor 4 showed about 0.13 V at a time point when the temperature had reached 80° C. As apparent from FIGS. 3 and 4, this output signal corresponds to 30 mg/dl which is the protein concentration of the urine.

According to this example, by mixing an acid into the sample to be detected, and thereby slightly acidifying it to a pH of about 4.1, it was possible to clear even the urine opacified by precipitation of phosphate by dissolving the phosphate. Consequently, it was also possible to measure the protein concentration while ensuring the dynamic range for the urine opacified by precipitation of phosphate.

Incidentally, in this example, there was shown the example in which into 10 ml of the sample to be detected, was mixed about 0.5 ml of an aqueous solution of potassium hydrogenphthalate with a molar concentration of 0.5 M (mol/L). However, by mixing the aqueous solution of potassium hydrogenphthalate into the sample to be detected even in other concentrations and mixing ratios to slightly acidify it to a pH of from about 4.0 to 4.5, it is possible to dissolve the phosphate to clear the sample solution.

Further, in this example, a description has been given to the urine opacified by precipitation of phosphate. However, for the urine opacified by precipitation of carbonate, by mixing the aqueous solution of potassium hydrogenphthalate therein to slightly acidify it to a pH of from about 4.0 to 4.5 in the same manner, it is also possible to dissolve the carbonate, and thereby clear the urine.

Further, in this example, there was shown the example in which the aqueous solution of potassium hydrogenphthalate was used. However, by mixing a weak acid such as acetic acid, citric acid, or ascorbic acid into the sample to be detected, and thereby slightly acidifying the sample to a pH of about 4.3 to 5.5, it is possible to dissolve the phosphate or carbonate, and thereby clear the sample, so that the same effects can be exhibited.

EXAMPLE 6

In this example, a calibration line of FIG. 3 obtained in Example 1 was formed in a different manner from as in Example 1.

From the ratio of scattered light intensities at 65° C. and 75° C., i.e., the ratio of output signals from the photosensor 4 at 65° C. and 75° C. in FIG. 3, the calibration line with respect to the protein concentration was formed. This ratio is represented by, for example, "r" calculated from the following formula (3):

$$r = \text{(output signal from the photosensor 4 at 75° C.)/(output signal from the photosensor 4 at 65° C.)} \quad (3)$$

For example, "r" for the urine having a protein concentration of about 30 mg/dl, prepared by adding albumin thereto, and indicated with the bold solid line of FIG. 3 was about 4.8 (0.116/0.024). Then, each "r" for the urines of which protein concentrations had been measured to be 12, 63, and 99 mg/dl, and "r" for the urine having a protein concentration of 1 mg/dl or less, which was used when the urine having a protein concentration of about 30 mg/dl was prepared by adding albumin thereto were calculated. Namely, the values of "r" were calculated for a total of five types of the samples to be detected. The results are shown in FIG. 5.

Figure 5:
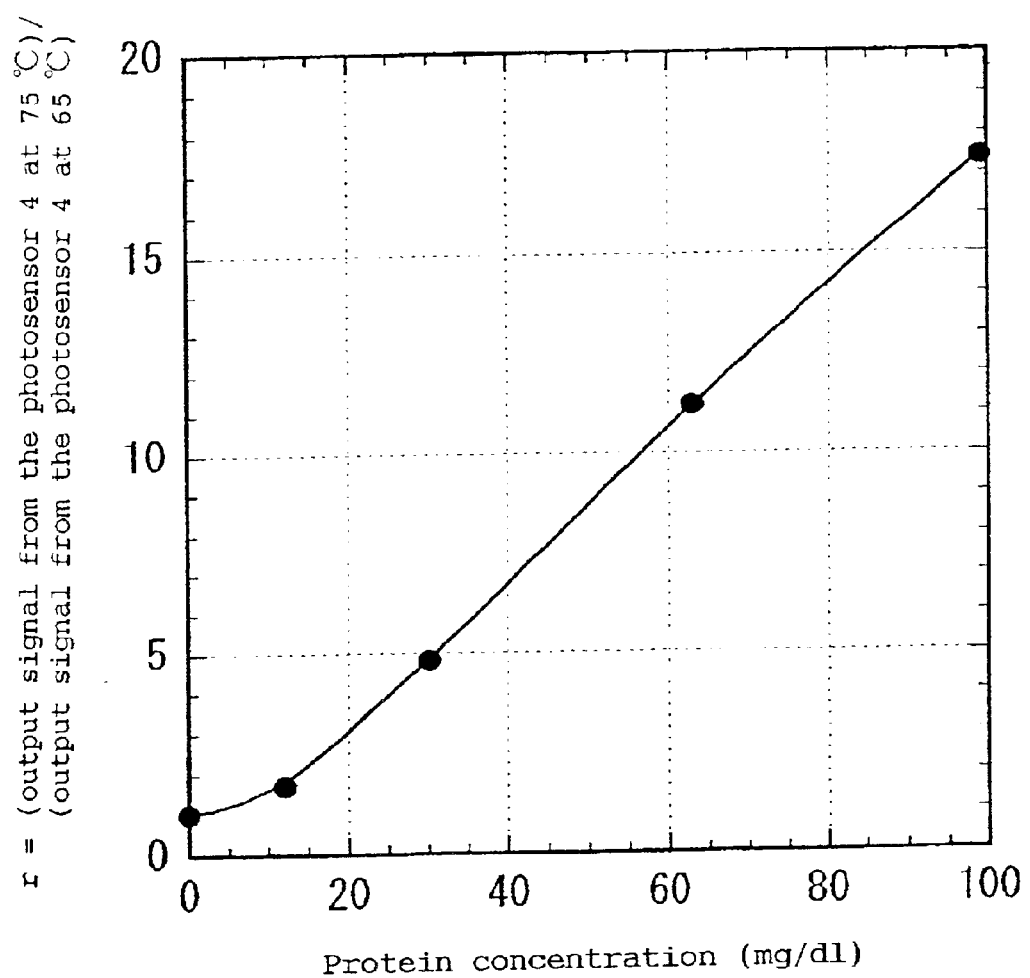
FIG. 5 is a graph showing the relation between an output signal ratio (r) and a protein concentration.

In FIG. 5, the five points were joined to obtain a solid line. The protein concentration can be measured by using the regression line indicated with this solid line as a calibration line.

As in this example, by mixing an acid into the samples to be detected, acidifying them to reduce the variations in pH, and thereby substantially equalizing the opacification starting temperatures, it is possible to measure the protein concentrations without being affected by the original pHs of the samples to be detected. When the concentration is calculated from the ratio of the scattered light intensities at respective temperatures as in this example, the opacification starting temperature can be effectively fixed independently of the pH is especially effective.

Further, the measurement of the protein concentration from the ratio of the scattered light intensities as in this example is less likely to be affected by the difference in transmittance of the urine before heating. Further, it can also reduce the opacity due to the portion of the phosphate, or carbonate which has remained undissolved even by the weak acidification thereof, the opacity due to precipitation of the other substance than the phosphate and the carbonate, and the influence due to the materials in the urine, such as mucin, and therefore it has a higher reliability.

Incidentally, the ratio of the scattered light intensities at 65° C. and 75° C. was used as "r" as shown in the formula (3) in this example. However, it is also acceptable to use the ratio of the scattered light intensities at temperatures between the other opacification starting temperatures and 80° C. Further, although there was shown the example in which potassium hydrogenphthalate was used as an acid, the same effects can be obtained even when acetic acid, citric acid, or ascorbic acid is used.

EXAMPLE 7

In this example, before heating the sample to be detected, the angle of rotation thereof was measured at ordinary temperature. Then, the temperature of the sample to be detected and the intensity of a light transmitting therethrough were measured while heating it. By measuring the angle of rotation, it was possible to obtain information about the spontaneous optical active substance in the sample to be detected. Especially in a urinalysis, it became possible to calculate the urine sugar value in addition to the urine protein value. Namely, since the optical rotation of the urine is considered to be the sum of the one attributed to glucose and the one attributed to albumin in the urine as described above, it was possible to calculate the urine sugar value from the urine protein value and the angle of rotation obtained by opacifying the urine.

The measuring apparatus used in this example is shown in FIG. 6. In FIG. 6, the projector module 1 serving as a light source is the same as used in Example 1, and it projects the substantially parallel light 2 having a wavelength of 670 nm and an intensity of 5 mW. A polarizer 10 transmits only a component in a specific direction out of the projected light. An analyzer 11 is arranged with the polarizer 10 in a crossed nicols state, and can be rotated about the transmission axis of the polarizer 10 as its rotation axis. A sample cell 12 for accommodating the sample to be detected is so configured that a solenoid coil 13 is wound therearound so that a magnetic field can be applied along the advancing direction of the substantially parallel light 2 on the sample to be detected, the substantial optical path length is 50 mm, and the prescribed volume is 10 ml. With this configuration, the polarization direction of the substantially parallel light 2 is controlled while being modulated by controlling the current to be passed through the solenoid coil 13 while modulating it by using the optical Faraday effect of the sample to be detected.

Incidentally, the basic principle of the method for measuring the angle of rotation by the Faraday effect of the sample to be detected itself in this manner is described in Japanese Laid-Open Patent Publication No.Hei 9-145605.

The apparatus shown in FIG. 6 includes an inlet port 14 for mixing an acid into the sample cell 12, and a vent hole 15 for air to go in and out. A photosensor 16 detects the substantially parallel light 2 transmitted through the analyzer 11.

Herein, when the polarizer 10 and the analyzer 11 are ideal ones, i.e., the extinction ratio is infinite, and the polarization direction of the substantially parallel light 2 is not rotated in the sample to be detected, the transmitted light does not reach the photosensor 16. However, in actuality, the extinction ratio of the polarizer and the analyzer does not become infinite. Since the extinction ratio of the polarizer 10 and the analyzer 11 used in this example is about 5000, a transmitted light of about 1 $\mu$W reaches the photosensor 16. The intensity of the light is enough for measuring the transmitted light intensity.

Further, the apparatus includes a coil driver 18 for controlling the current to be injected into the solenoid coil, and a signal generator 19 for supplying a modulation signal for modulating the current to be injected into the solenoid coil to the coil driver 18. Further, it has a lock-in amplifier 17 for performing a phase sensitive detection on an output signal from the photosensor 16 by using the modulation signal of the solenoid coil as a reference signal. When the angle of rotation of the sample to be detected is measured, a computer 20 supplies a control current signal to the coil driver 18 so that the output signal from the lock-in amplifier 17 becomes zero.

In case of this example, a modulation current with an amplitude of 0.001 (A), and a frequency of 1.3 KHz is passed through the solenoid coil. Consequently, the control current signal for making the output signal from the lock-in amplifier 17 zero, i.e., the compensation control current is found to calculate the angle of rotation. Herein, there was used the method for determining the angle of rotation by the control current signal, which provides such a magnetic field that the angle of rotation arisen from optical active substances such as protein and glucose in the sample to be detected is in agreement with the angle of rotation of the polarization direction due to the Faraday effect of the solvent of the sample to be detected by the application with a magnetic field.

There is also provided a pipette 21 for injecting a prescribed amount of a reagent through a tube 22 from the inlet port 14 into the sample to be detected in the sample cell 12. The computer 20 also controls the projector module 1 serving as a light source, and the pipette 21, and analyzes the output signal from the lock-in amplifier 17. At this step, the computer 20 supplies the output signal from the signal generator 19 to the projector module 1, and intensity-modulates the substantially parallel light 2 with the output signal from the signal generator 19. At this step, the lock-in amplifier 17 performs a phase sensitive detection on the output signal from the photosensor 16 with reference to the modulation signal issued from the signal generator 19 to the projector module 1 serving as a light source. The output signal from the lock-in amplifier 17 corresponds to the transmitted light intensity. The results measured at a temperature sensor 23 for measuring the temperature of the sample to be detected in the sample cell 12 are analyzed at the computer 20.

The glucose concentration of the urine, which is the solution to be detected, i.e., the urine sugar value and the urine protein concentration were detected by using the apparatus in accordance with this example.

First, 10 ml of the sample to be detected was introduced into the sample cell 12. The computer 20 operated the projector module 1 and the coil driver 18. At this step, the substantially parallel light 2 was not subjected to intensity modulation. In this state, the angle of rotation of the sample to be detected was measured. Then, the computer 20 stopped the operation of the coil driver 18, and at the same time, it supplied the modulation signal to the projector module 1 to intensity-modulate the substantially parallel light 2. Then, it started the monitoring of the output signal from the lock-in amplifier 17.

Then, the computer 20 controlled the pipette 21, so that 0.5 ml of an aqueous solution of potassium hydrogenphthalate with a concentration of 0.5 M was mixed from the inlet port 14 into the sample cell 12. Then, a current was passed through the solenoid coil 13, so that the sample to be detected was heated together with the sample cell 12. At this step, the computer 20 controlled the coil driver 18 based on the output signal from the temperature sensor 23 to heat it from 35° C. to 80° C. at a heating rate of 25° C./min. This heating pattern is shown with a dotted line of FIG. 10.

Herein, when the heating rate exceeded 25° C./min, the temperature distribution at the time of heating was increased, and a part of the sample reached the boiling point, so that the optical path was obstructed by vapor bubbles arisen. Accordingly, it became impossible to carry out the measurement. Therefore, it has been indicated that, when the sample was heated up to 80° C., the upper limit of the heating rate was 25° C./min. Then, the protein concentration was measured from the output signal from the lock-in amplifier when the temperature had reached 80° C. Namely, the protein concentration was measured at a time point indicated with a measurement point 2 in the heating measurement pattern indicated with the dotted line of FIG. 10.

Figure 7:
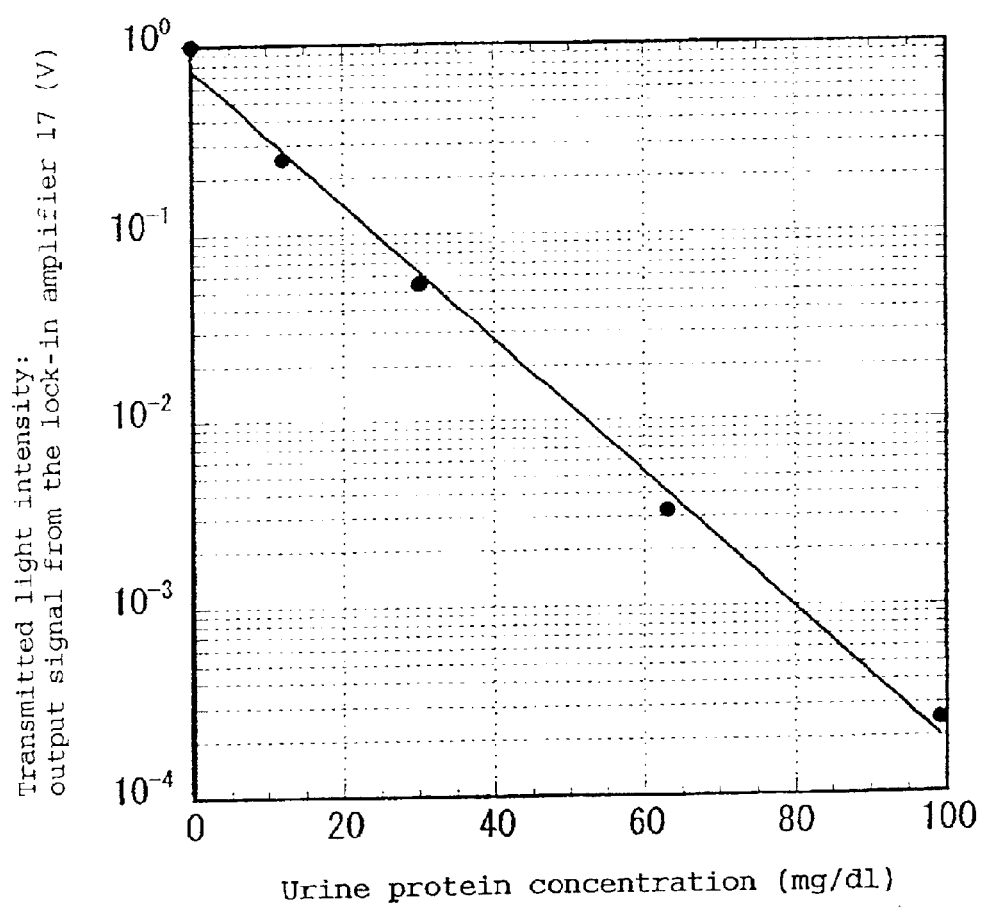
FIG. 7 is a graph showing the relation between a transmitted light intensity and a urine protein concentration.

Herein, a calibration line showing the protein concentration was formed by using the sample to be detected, used in forming the graph of FIG. 4. The resulting calibration line is shown in FIG. 7. In FIG. 7, the abscissa denotes the protein concentration, and the ordinate denotes the transmitted light intensity when the temperature has reached 80° C., i.e., the output signal from the lock-in amplifier 17.

The measurement was carried out on the urine with a urine sugar value of 100 mg/dl, a urine protein concentration of 15 mg/dl, and a pH of 7.0 as a sample to be detected. As a result, the angle of rotation was found to be about 0.0034. Herein, the specific rotatory power of glucose at this wavelength (670 nm) was about 40° (deg/cm·dl/kg). Therefore, if it is assumed that this angle of rotation is totally occurred due to glucose, the glucose concentration, i.e., the urine sugar value nearly equals 85 (mg/dl). However, the specific rotatory power of protein was found to be about −40° (deg/cm·dl/kg). Namely, since the signs are opposite, but the absolute values are the same, it is converted to be 100−15= 85 (mg/dl) in terms of glucose concentration. Thus, it has been confirmed that the measurement was carried out with precision.

The output signal from the lock-in amplifier 17 when the temperature has reached 80° C. by mixing an aqueous solution of potassium hydrogenphthalate therein, and heating the mixture, was found to be 0.22 V. The protein concentration was estimated from this value based on the calibration line of FIG. 7 to be 15 mg/dl. Thus, it has been confirmed that that the measurement was carried out with precision.

According to this example, by measuring the angle of rotation of the sample to be detected, and the concentration of the spontaneous optical active substance, mixing an acid therein, and heating it up to 80° C., it was possible to measure the protein concentration. Herein, since the sample to be detected was heated by passing a current though the solenoid coil utilized in measuring the angle of rotation, it was also possible to achieve the simplification of the apparatus. Further, by modulating the intensity of the substantially parallel light 2 to perform a phase sensitive detection on the output signal from the photosensor at the lock-in amplifier, it was also possible to detect even the light with a very minute intensity transmitted through the analyzer present at a crossed nicols site, thereby to measure the protein concentration with precision.

This example shows that the practical utility thereof is high especially when the sample to be detected is a urine. The reason for this will be described below.

When the urine protein concentration is normal, glucose is predominant as the spontaneous optical active substance in the urine. Therefore, the urine sugar value can be detected by measuring the angle of rotation of the urine. In this case, the urine protein concentration measurement carried out by measuring methods other than the method of polarimetry is more reliable. The reason for this is as follows. Since protein is also a spontaneous optical active substance, the angle of rotation obtained by adding the angle of rotation occurred due to glucose with the angle of rotation occurred due to protein is observed as the angle of rotation of the urine. Then, as described above, by heating the urine up to 80° C. after mixing an acid therein, measuring the protein concentration, and determining the concentration, the measured result of the angle of rotation can be corrected. Then, the urine sugar value and the urine protein concentration can be determined.

Herein, various metal salts such as calcium salt are present in the urine. Upon heating them up to 80° C. or more, they become more likely to adhere to the inside of the sample cell. Therefore, by restricting the heating temperature down to 80° C. or less, it is possible to reduce the contamination due to the adhesion. Further, since the temperature difference from the boiling point is large, the restriction on the temperature distribution arising upon heating for preventing bumping can be reduced. Further, the temperature difference is large, and as a result, it becomes possible to improve the heating rate, resulting in a reduction in measurement time.

As in this example, since an acid is mixed in the urine and the mixture is heated after measuring the angle of rotation, both the glucose and protein can be measured. The reason for this is as follows. Upon mixing an acid in the urine and heating the mixture, the protein component coagulates, and in some cases, it becomes impossible for a light to transmit through the inside of the sample to be detected. Further, the angle of rotation occurred due to protein may change by modification of the protein.

EXAMPLE 8

In this example, the calibration line shown in FIG. 7 obtained in Example 7 was formed by using the apparatus shown in FIG. 6 with a different method from that of Example 7.

First, the following solution was prepared by using a urine having a pH of 6.1, of which the protein concentration had been previously judged as being not more than 1 mg/dl by a dye coupling method (pyrogallol red/molybdenum complex coloring method) as a solvent. First, 100 mg of albumin was weighed to be charged in a 1-dl measuring flask, and the urine was charged therein to prepare a urine solution with a total volume of 1 dl. The protein concentration of the urine solution was about 100 mg/dl. Expressing it more precisely, the protein concentration thereof was from 100 to 101 mg/dl. Whereas, the pH thereof was 5.8.

Similarly, four types of urines with different pHs, of which the protein concentration had been previously judged as being not more than 1 mg/dl were used as solvents to prepare urine solutions with a concentration of 100 mg/dl. Their respective pHs were 5.1, 6.4, 7.1, and 8.1. The five types of urines with a protein concentration of about 100 mg/dl and pHs of 5.1, 5.8, 6.4, 7.1, and 8.1 were respectively introduced each in an amount of 10 ml into the sample cell 3, and about 0.5 ml of an aqueous solution of potassium hydrogenphthalate with a molar concentration of 0.5 M (mol/L) was mixed in each of the urines. At this step, the pHs of the urines whose pHs before mixing had been respectively 5.1, 5.8, 6.4, 7.1, and 8.1 became 4.1, 4.2, 4.2, 4.3, and 4.3 after mixing, respectively.

Figure 8:
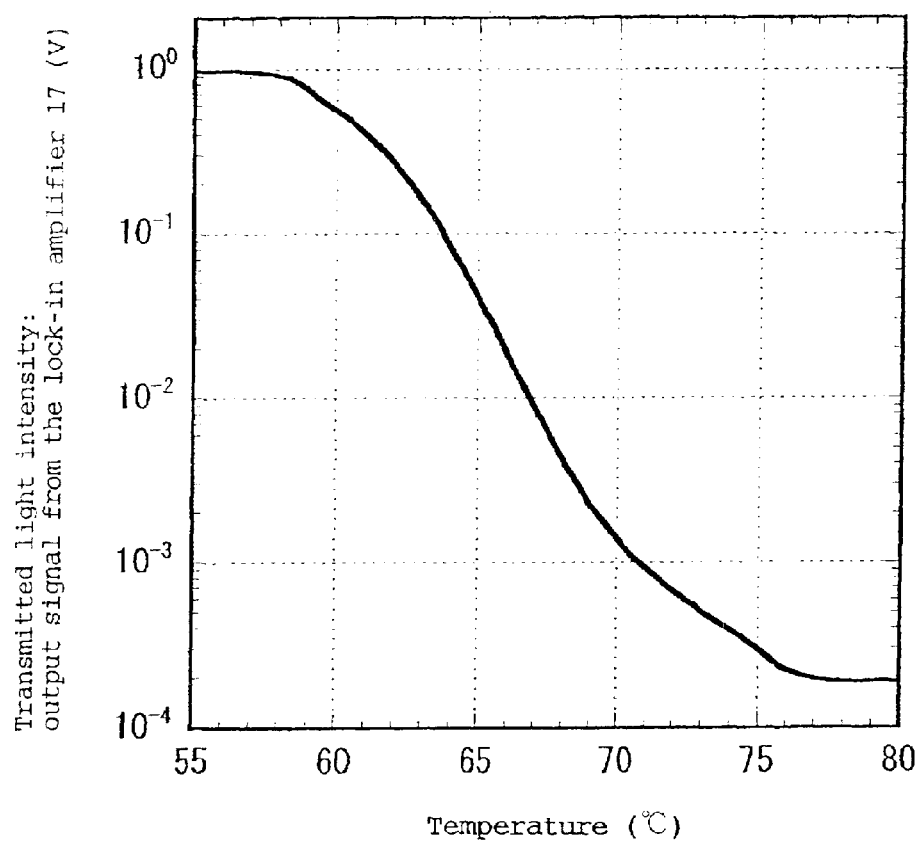
FIG. 8 is a graph showing the relation between a transmitted light intensity and temperature.

The samples to be detected were heated from 35° C. to 80° C. at a heating rate of 25° C./min in the same manner as in Example 7. FIG. 8 shows the variations in output signal from the lock-in amplifier 17 at this step. The urines with 5 types of pHs are all indicated with one solid line in FIG. 8.

A calibration line with respect to the protein concentration was formed from the ratio of transmitted light intensities at 62° C. and 72° C. in FIG. 8, i.e., the ratio of output signal from the lock-in amplifier 17 at 62° C. and 72° C. This ratio is represented by, for example, "R" calculated from the formula (4):

$$R = \text{(output signal from the lock-in amplifier \textbf{17} at } 62° \text{ C.)/(output signal from the lock-in amplifier \textbf{17} at } 72° \text{ C.)} \quad (4)$$

For example, "R" for the urine with a protein concentration of about 100 mg/dl, indicated with the solid line of FIG. 8 is about $2.5 \times 10^{-1}/6.2 \times 10^{-4} \approx 4.0 \times 10^{2}$.

Further, each "R" for the urines of which protein concentrations had been measured to be 12, 30, 63, and 99 mg/dl, and "R" for the urine having a protein concentration of 1 mg/dl or less which was used in preparing the urine having a protein concentration of about 100 mg/dl by adding albumin thereto were calculated. Namely, the values of "R" were calculated for a total of five types of the samples to be detected. The results are shown in FIG. 9.

Figure 9:
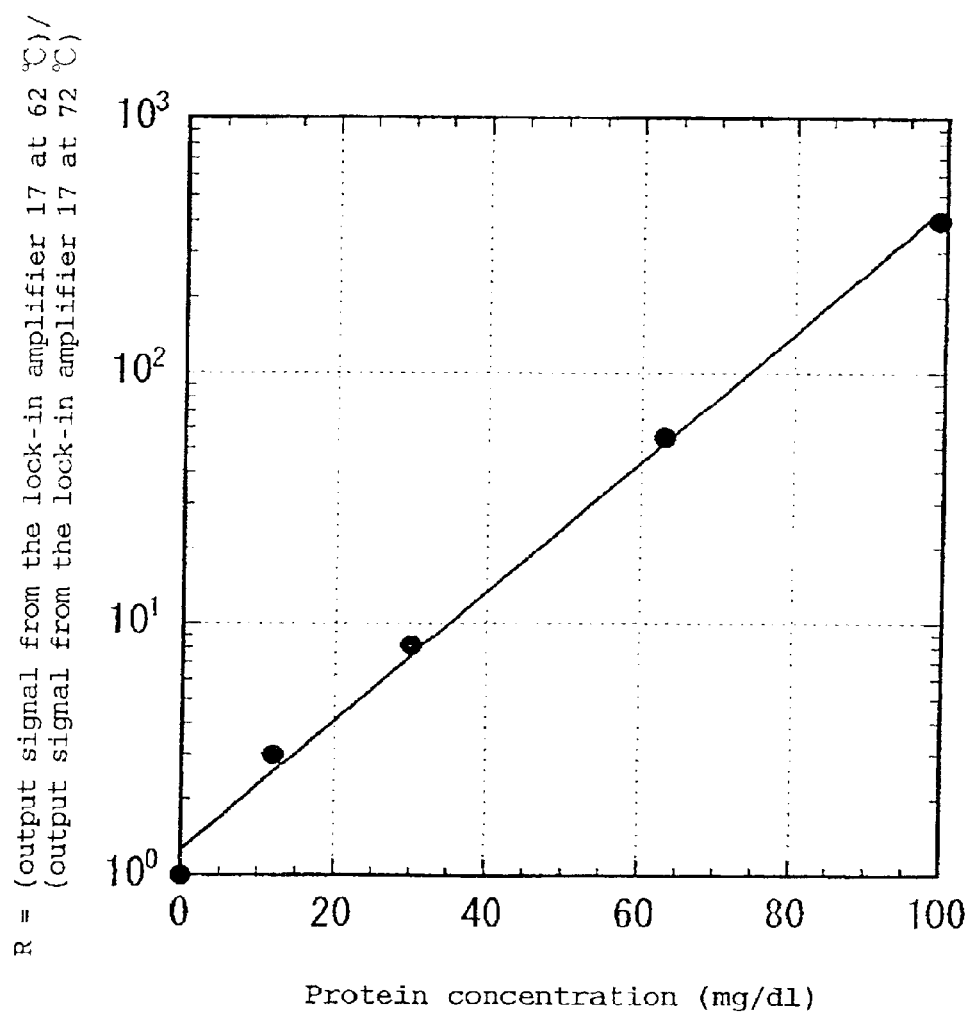
FIG. 9 is a graph showing the relation between an output signal ratio (R) and a protein concentration.

In FIG. 9, the five points were joined to obtain a solid line. The protein concentration can be measured by using the solid line as a calibration line.

Then, the measurement was carried out on the urine with a urine sugar value of 100 mg/dl, a urine protein concentration of 15 mg/dl, and a pH of 7.0 as a sample to be detected.

As a result, the angle of rotation of the urine was found to be about 0.0034°. Herein, the specific rotatory power of glucose at this wavelength (670 nm) was about 40 (deg/cm·dl/kg). Therefore, if it is assumed that this angle of rotation is totally occurred due to glucose, the glucose concentration, i.e., the urine sugar value becomes about 85 (mg/dl). However, the specific rotatory power of protein was found to be about −40° (deg/cm·dl/kg). Namely, since the signs are opposite, but the absolute values are the same, if it is converted into the glucose concentration, the glucose concentration is 100−15=85 (mg/dl). Thus, it has been confirmed that the measurement was carried out with precision.

An aqueous solution of potassium hydrogenphthalate was mixed therein, and the mixture was heated up to 80° C. at a heating rate of 25° C./min to calculate "R" from the formula (4). R was found to be 3. The protein concentration was estimated from this value based on the calibration line of FIG. 9 to be 15 mg/dl. Thus, it has been confirmed that that the measurement was carried out with precision.

According to this example, by measuring the angle of rotation of the sample to be detected, thereby measuring the concentration of the spontaneous optical active substance, and mixing an acid therein, and heating the mixture up to 80° C., it was possible to measure the protein concentration.

As in this example, by mixing an acid in the sample to be detected to acidify it, so that variations in pH are reduced, and thereby substantially equalizing the opacification starting temperatures, it is possible to measure the protein concentration without being affected by the original pH of the sample to be detected. When the concentration is calculated from the ratio of transmitted light intensities at respective temperatures as in this example, such fixation of the opacification starting temperature independent of the pH is especially effective.

Further, the measurement of the protein concentration from the ratio of the transmitted light intensities as in this example is less likely to be affected by the difference in transmittance of the urine before heating. Further, it can also reduce the opacity due to the portion of the phosphate or carbonate which has remained undissolved even by the slight acidification thereof, opacity due to precipitation of the other substances than the phosphate and the carbonate, and the influence due to the materials in the urine, such as mucin, and therefore it has a higher reliability.

Incidentally, the ratio of the scattered light intensities at 62° C. and 72° C. was used as R as shown in the formula (4) in this example. However, it is also acceptable to use the ratio between other temperatures. Further, although there was shown the example in which potassium hydrogenphthalate was used as an acid, the same effects can be obtained even when acetic acid, citric acid, or ascorbic acid is used.

Although the heating rate was assumed to be 25° C./min, the same effects can be obtained by forming a calibration line with respect to respective heating rates even at other heating rates. At this step, if the heating rate is improved in such a range that the temperature distribution at the time of heating is allowable, the measurement time can be reduced.

As described above, in the present invention, an acid is mixed in a sample to be detected containing protein, such as a urine, and then the mixture is heated to be opacified. A light is then projected on the sample to measure the intensity of the light transmitted through the sample, or the light scattered from the sample. Consequently, it is possible to evaluate the protein concentration of the sample with an extraordinarily high pH with high precision.

Further, the heating temperature can be reduced, and the contamination of the sample cell due to metal salts, and the like can be reduced. Still further, even if phosphate, carbonate, and the like are precipitated, the sample can be cleared by dissolving them, so that the protein concentration can be measured with high precision. The present invention can also provide a method of urinalysis in which consumable items such as a test paper are not used.

Although the present invention has been described in terms of the presently preferred embodiments, it is to be understood that such disclosure is not to be interpreted as limiting. Various alterations and modifications will no doubt become apparent to those skilled in the art to which the present invention pertains, after having read the above disclosure. Accordingly, it is intended that the appended claims be interpreted as covering all alterations and modifications as fall within the true spirit and scope of the invention.

What is claimed is:

1. A method for measuring a concentration of a solution comprising the steps of: (1) mixing an acid in a sample to be detected containing at least protein; (2) heating and opacifying said sample to be detected with said acid mixed; (3) projecting a light on the opacified sample to be detected; (4) detecting a light transmitted through said sample to be detected and/or a light scattered from said sample to be detected out of the projected light; and (5) determining a protein concentration of said sample to be detected based on an intensity of the detected light, wherein said step (2) and said step (3) are performed simultaneously, wherein said opacified sample to be detected contains a spontaneous optical active substance other than protein, said method further comprising a step of: measuring an angle of rotation of said spontaneous optical active substance and said protein in said sample to be detected before mixing said acid in said sample to be detected, and determining a concentration of said spontaneous optical active substance in said sample to be detected.

2. A method for measuring a concentration of a solution comprising the steps of: (1) mixing an acid in a sample to be detected containing at least protein; (2) heating and opacifying said sample to be detected with said acid mixed; (3) projecting a light on the opacified sample to be detected; (4) detecting a light transmitted through said sample to be detected and/or a light scattered from said sample to be detected out of the projected light; and (5) determining a protein concentration of said sample to be detected based on an intensity of the detected light, wherein said step (2) and said step (3) are performed simultaneously, wherein said light transmitted through said sample to be detected and/or the light scattered from said sample to be detected are detected at two mutually different temperatures to determine the concentration of protein in said sample to be detected from an intensity ratio of the transmitted lights and/or an intensity ratio of the scattered lights.

3. A method for measuring a concentration of a solution comprising the steps of: (1) mixing an acid in a sample to be detected containing at least protein; (2) heating and opacifying said sample to be detected with said acid mixed; (3) projecting a light on the opacified sample to be detected; (4) detecting a light transmitted through said sample to be detected and/or a light scattered from said sample to be detected out of the projected light; and (5) determining a protein concentration of said sample to be detected based on an intensity of the detected light, wherein said step (2) and said step (3) are performed simultaneously, wherein the heating temperature is not less than a temperature at which said sample to be detected starts to be opacified, and not more than 80° C.

4. A method for measuring a concentration of a solution comprising the steps of: (1) mixing an acid in a sample to be detected containing at least protein; (2) heating and opacifying said sample to be detected with said acid mixed; (3) projecting a light on the opacified sample to be detected; (4) detecting a light transmitted through said sample to be detected and/or a light scattered from said sample to be detected out of the projected light; and (5) determining a protein concentration of said sample to be detected based on an intensity of the detected light, wherein said step (2) and said step (3) are performed simultaneously, wherein a calibration line with respect to the protein concentration is formed for every heating measurement pattern comprising a temperature at which heating of the sample to be detected is started, a heating rate, a heating completion temperature, a duration of time that the heating temperature is held constant, and a time point at which the transmitted light intensity and the scattered light intensity are measured.

5. A method for measuring a concentration of a solution comprising the steps of: (1) mixing an acid in a sample to be detected containing at least protein; (2) heating and opacifying said sample to be detected with said acid mixed; (3) projecting a light on the opacified sample to be detected; (4) detecting a light transmitted through said sample to be detected and/or a light scattered from said sample to be detected out of the projected light; and (5) determining a protein concentration of said sample to be detected based on an intensity of the detected light, wherein said step (2) and said step (3) are performed simultaneously, wherein a rate for heating said sample to be detected is set such that a maximum temperature portion in the sample to be detected due to the temperature distribution in heating is not more than the boiling point of the sample to be detected.

6. The method for measuring a concentration of a solution in accordance with claim 5, wherein when said maximum temperature portion in the sample to be detected due to the temperature distribution in heating is not more than the boiling point of the sample to be detected, said rate for heating the sample to be detected is set at the maximum to reduce the measurement time.

7. A method for measuring a concentration of a solution comprising the steps of: (1) mixing an acid in a sample to be detected containing at least protein; (2) heating and opacifying said sample to be detected with said acid mixed; (3) projecting a light on the opacified sample to be detected; (4) detecting a light transmitted through said sample to be detected and/or a light scattered from said sample to be detected out of the projected light; and (5) determining a protein concentration of said sample to be detected based on an intensity of the detected light, wherein said step (2) and said step (3) are performed simultaneously, wherein said acid is mixed in the sample to be detected to acidify the sample to be detected to a pH of less than 7.0.

8. A method for measuring a concentration of a solution comprising the steps of: (1) mixing an acid in a sample to be detected containing at least protein; (2) heating and opacifying said sample to be detected with said acid mixed; (3) projecting a light on the opacified sample to be detected; (4) detecting a light transmitted through said sample to be detected and/or a light scattered from said sample to be detected out of the projected light; and (5) determining a protein concentration of said sample to be detected based on an intensity of the detected light, wherein said step (2) and said step (3) are performed simultaneously, wherein said acid is mixed in the sample to be detected to weakly acidify the sample to be detected to a pH of from 4.0 to 5.3.

9. A method for measuring a concentration of a solution comprising the steps of: (1) mixing an acid in a sample to be detected containing at least protein; (2) heating and opacifying said sample to be detected with said acid mixed; (3) projecting a light on the opacified sample to be detected; (4) detecting a light transmitted through said sample to be detected and/or a light scattered from said sample to be detected out of the projected light; and (5) determining a protein concentration of said sample to be detected based on an intensity of the detected light, wherein said step (2) and said step (3) are performed simultaneously, wherein said acid is used in a solution form, and the concentration of the acid solution is in a saturated state in the temperature range used in said method for measuring the concentration of a solution.

10. The method for measuring a concentration of a solution in accordance with claim 9, wherein said step (1) is performed before said step (2).

11. A method for measuring a concentration of a solution comprising the steps of: (1) mixing an acid in a sample to be detected containing at least protein; (2) heating and opacifying said sample to be detected with said acid mixed; (3) projecting a light on the opacified sample to be detected; (4) detecting a light transmitted through said sample to be detected and/or a light scattered from said sample to be detected out of the projected light; and (5) determining a protein concentration of said sample to be detected based on an intensity of the detected light, wherein said step (2) and said step (3) are performed simultaneously, wherein said sample to be detected is a urine which includes a spontaneous optical active substance, and said spontaneous optical active substance is glucose.

12. The method of urinalysis in accordance with claim 11, wherein a light with a wavelength of 500 nm or more is used.

13. A method for measuring a concentration of a solution comprising the steps of: (1) mixing an acid in a sample to be detected containing at least protein; (2) heating and opacifying said sample to be detected with said acid mixed; (3) projecting a light on the opacified sample to be detected; (4) detecting a light transmitted through said sample to be detected and/or a light scattered from said sample to be detected out of the projected light; and (5) determining a protein concentration of said sample to be detected based on an intensity of the detected light, wherein said opacified sample to be detected contains a spontaneous optical active substance other than protein, said method further comprising a step of: measuring an angle of rotation of said spontaneous optical active substance and said protein in said sample to be detected before mixing said acid in said sample to be detected, and determining a concentration of said spontaneous optical active substance in said sample to be detected.

14. A method of urinalysis using said method for measuring concentration of a solution in accordance with claim 13, wherein said sample to be detected is a urine, and said spontaneous optical active substance is glucose.

15. The method of urinalysis in accordance with claim 14, wherein a light with a wavelength of 500 nm or more is used.

16. A method for measuring a concentration of a solution comprising the steps of: (1) mixing an acid in a sample to be detected containing at least protein; (2) heating and opacifying said sample to be detected with said acid mixed; (3) projecting a light on the opacified sample to be detected; (4) detecting a light transmitted through said sample to be detected and/or a light scattered from said sample to be detected out of the projected light; and (5) determining a protein concentration of said sample to be detected based on an intensity of the detected light, wherein said acid is mixed in the sample to be detected to weakly acidify the sample to be detected to a pH of from 4.0 to 5.3.

17. A method of urinalysis using said method for measuring concentration of a solution in accordance with claim 16, wherein said sample to be detected is a urine which includes a spontaneous optical active substance, and said spontaneous optical active substance is glucose.

18. The method of urinalysis in accordance with claim 17, wherein a light with a wavelength of 500 nm or more is used.

19. A method for measuring a concentration of a solution comprising the steps of: (1) mixing an acid in a sample to be detected containing at least protein; (2) heating and opacifying said sample to be detected with said acid mixed; (3) projecting a light on the opacified sample to be detected; (4) detecting a light transmitted through said sample to be detected and/or a light scattered from said sample to be detected out of the projected light; and (5) determining a protein concentration of said sample to be detected based on an intensity of the detected light, wherein said acid is used in a solution form, and the concentration of the acid solution is in a saturated state in the temperature range used in said method for measuring the concentration of a solution, wherein said sample to be detected is a urine which includes a spontaneous optical active substance, and said spontaneous optical active substance is glucose.

20. The method of urinalysis in accordance with claim 19, wherein a light with a wavelength of 500 urn or more is used.

* * * * *